(12) United States Patent
Carson et al.

(10) Patent No.: US 6,225,082 B1
(45) Date of Patent: May 1, 2001

(54) MYELIN BASIC PROTEIN MRNA TRANSPORT AND TRANSLATION ENHANCER SEQUENCES

(75) Inventors: John Carson, West Hartford; Sunjong Kwon, Newington, both of CT (US); Kevin Ainger; Daniela Avossa, both of Zurich (CH)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

(21) Appl. No.: 08/853,980

(22) Filed: May 9, 1997

(51) Int. Cl.[7] .................. C12N 15/67; C12N 15/11; C12N 15/63; C12N 5/10
(52) U.S. Cl. ............... 435/69.1; 435/320.1; 435/325; 536/24.1
(58) Field of Search ............... 435/69.1, 320.1, 435/325; 514/44; 536/23.1, 24.1

(56) References Cited

PUBLICATIONS

Orkin et al. Report and Recommendations of the Panel to Assess the NIH Investment in Research on Gene Therapy, pp. 1–41, 1995.*
Pines GFP in mammalian cells. Trends in Genetics vol. 11 pp. 326–327, 1995.*
Alam et al. Reporter Genes: Application to the study of Mammalian Gene Transcription. Analytical Biochemistry vol. 188 pp. 245–254, 1990.*
Ainger et al. Transport and localization elements i myelin basic protein mRNA. J. Cell Biology vol. 138 pp. 1077–1087, 1997.*
Roach et al. Characterization of cloned cDNA representing rat myelin basic protein: absence of expression in brain of shiverer mutant mice. Cell vol. 34 pp. 799–806, 1983.*
Gura et al. Systems for identifying new drugs are often faulty. Science vol. 278 pp. 1041–1042, 1997.*

* cited by examiner

Primary Examiner—John S. Brusca
(74) Attorney, Agent, or Firm—Scully, Scott, Murphy & Presser

(57) ABSTRACT

The present invention provides isolated nucleic acid molecules which comprise sequences from the 3' UTR of myelin basic protein (MBP) mRNA. The subject isolated nucleic acid molecules confer properties such as localization, transport and increased translational efficiency of a heterologous mRNA transcript when transcribed into such mRNA. The present invention also provides vectors comprising the subject isolated nucleic acids. The vectors are useful for increasing translational efficiency of mRNA transcripts produced by a heterologous gene incorporated therein. Also provided by the present invention are methods for increasing translation of a heterologous gene. The methods comprise transforming a eukaryotic cell with at least one of the subject vectors having coding sequence for a heterologous gene. Methods for enhancing gene therapy are also provided.

27 Claims, 21 Drawing Sheets

(4 of 21 Drawing Sheet(s) Filed in Color)

Figure 3

In vivo Translation Assay

*in vitro* transcribed capped GFP mRNA

+

Texas Red-conjugated dextran microinjection into neuroblastoma B104 cells incubation at 37°C for 20-24 hours determining intensities of the expressed GFP/Texas Red using dual channel confocal microscopy

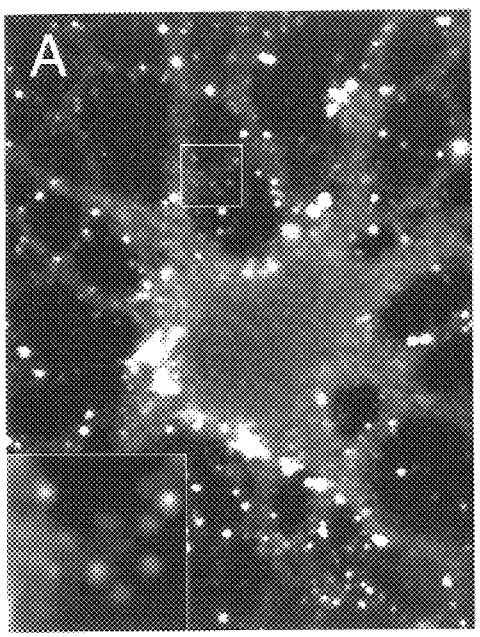 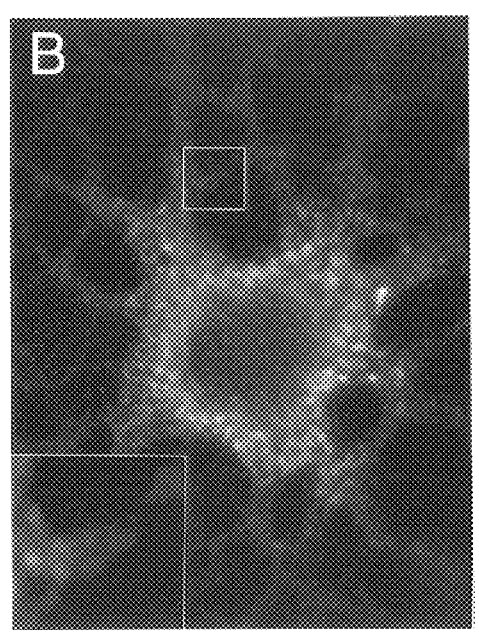
Figure 13A                    Figure 13B

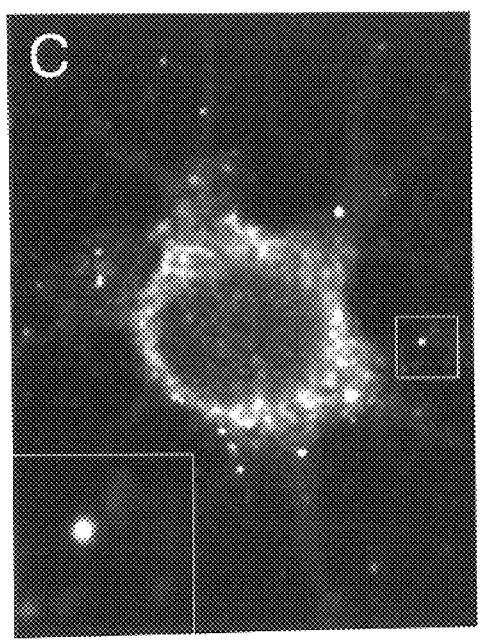 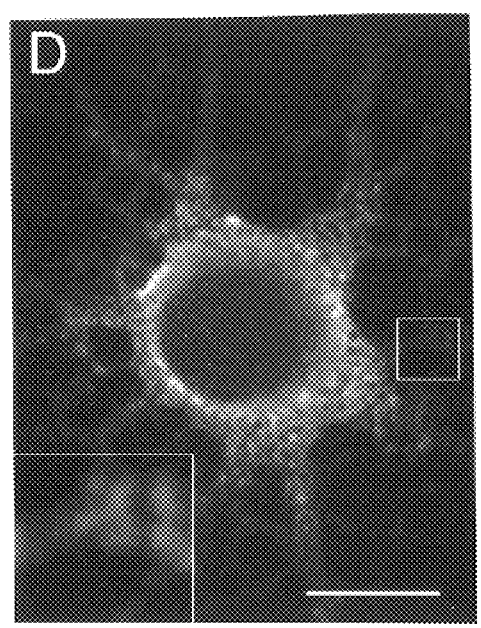
Figure 13C
Figure 13D

SEQUENCE LISTING

```
<160> NUMBER OF SEQ ID NOS: 30

<210> SEQ ID NO 1
<211> LENGTH: 8
<212> TYPE: RNA
<213> ORGANISM: Unknown
<220> FEATURE:
<223> OTHER INFORMATION: Description of Unknown Organism:  Myelin Basic
      protein consensus sequence

<400> SEQUENCE: 1 cuuusuuu                                                                    8

<210> SEQ ID NO 2
<211> LENGTH: 5
<212> TYPE: DNA
<213> ORGANISM: Unknown
<220> FEATURE:
<223> OTHER INFORMATION: Description of Unknown Organism:  localization
      motif

<400> SEQUENCE: 2 ggact                                                                       5

<210> SEQ ID NO 3
<211> LENGTH: 21
<212> TYPE: RNA
<213> ORGANISM: Unknown
<220> FEATURE:
<223> OTHER INFORMATION: Description of Unknown Organism:  rat and mouse
      MBP

<400> SEQUENCE: 3
gccaaggagc cagagagcau g                                                    21

<210> SEQ ID NO 4
<211> LENGTH: 20
<212> TYPE: RNA
<213> ORGANISM: Unknown
<220> FEATURE:
<223> OTHER INFORMATION: Description of Unknown Organism: human MBP RTS1

<400> SEQUENCE: 4
gccauggagg cacacagcug                                                      20

<210> SEQ ID NO 5
<211> LENGTH: 21
<212> TYPE: RNA
<213> ORGANISM: Unknown
```

```
<220> FEATURE:
<223> OTHER INFORMATION: Description of Unknown Organism: human MBP RTS2

<400> SEQUENCE: 5
gcugcagaga cagagaggac g                                              21

<210> SEQ ID NO 6
<211> LENGTH: 21
<212> TYPE: RNA
<213> ORGANISM: Unknown
<220> FEATURE:
<223> OTHER INFORMATION: Description of Unknown Organism: rat MOBP81A

<400> SEQUENCE: 6 accccccgaga cacagagcau g                                             21

<210> SEQ ID NO 7
<211> LENGTH: 21
<212> TYPE: RNA
<213> ORGANISM: Unknown
<220> FEATURE:
<223> OTHER INFORMATION: Description of Unknown Organism:  rat GFAP

<400> SEQUENCE: 7
gccaaggagc ccaccaaacu g                                              21

<210> SEQ ID NO 8
<211> LENGTH: 21
<212> TYPE: RNA
<213> ORGANISM: Unknown
<220> FEATURE:
<223> OTHER INFORMATION: Description of Unknown Organism:   human Ca-N

<400> SEQUENCE: 8
gccaaggagc gagagagggu g                                              21

<210> SEQ ID NO 9
<211> LENGTH: 21
<212> TYPE: RNA
<213> ORGANISM: Unknown
<220> FEATURE:
<223> OTHER INFORMATION: Description of Unknown Organism:  mouse MAP2A

<400> SEQUENCE: 9
gccaaggagu cagaagagau g                                              21

<210> SEQ ID NO 10
<211> LENGTH: 21
<212> TYPE: RNA
<213> ORGANISM: Unknown
<220> FEATURE:
<223> OTHER INFORMATION: Description of Unknown Organism: bovine
      GABAR(A)

<400> SEQUENCE: 10
gagagggagc cagagagcaa a                                              21

<210> SEQ ID NO 11
<211> LENGTH: 21
<212> TYPE: RNA
<213> ORGANISM: Unknown
<220> FEATURE:
<223> OTHER INFORMATION: Description of Unknown Organism:  bovine NOS

<400> SEQUENCE: 11
cacgaggagc cacagagcag a                                              21
```

<210> SEQ ID NO 12
<211> LENGTH: 21
<212> TYPE: RNA
<213> ORGANISM: Unknown
<220> FEATURE:
<223> OTHER INFORMATION: Description of Unknown Organism:  rat ARC

<400> SEQUENCE: 12
gcugaggagg aggagaucau u                                       21

<210> SEQ ID NO 13
<211> LENGTH: 21
<212> TYPE: RNA
<213> ORGANISM: Unknown
<220> FEATURE:
<223> OTHER INFORMATION: Description of Unknown Organism:  rat RC3

<400> SEQUENCE: 13
gccaaggacc cucaacaccg g                                       21

<210> SEQ ID NO 14
<211> LENGTH: 21
<212> TYPE: RNA
<213> ORGANISM: Unknown
<220> FEATURE:
<223> OTHER INFORMATION: Description of Unknown Organism: mouse
      protamine 2

<400> SEQUENCE: 14
gccaaggagc cacgagaucu g                                       21

<210> SEQ ID NO 15
<211> LENGTH: 21
<212> TYPE: RNA
<213> ORGANISM: Unknown
<220> FEATURE:
<223> OTHER INFORMATION: Description of Unknown Organism:  fugu NCAML1

<400> SEQUENCE: 15
gcccaggagc cagagaacau a                                       21

<210> SEQ ID NO 16
<211> LENGTH: 21
<212> TYPE: RNA
<213> ORGANISM: Unknown
<220> FEATURE:
<223> OTHER INFORMATION: Description of Unknown Organism: rat c-jun
      (AP-1)

<400> SEQUENCE: 16
ggcgaggagc cagagagcag c                                       21

<210> SEQ ID NO 17
<211> LENGTH: 21
<212> TYPE: RNA
<213> ORGANISM: Unknown
<220> FEATURE:
<223> OTHER INFORMATION: Description of Unknown Organism:rat rARP

<400> SEQUENCE: 17
gccgaggagc cagagagccc u                                       21

<210> SEQ ID NO 18
<211> LENGTH: 21
<212> TYPE: RNA

-continued

```
<213> ORGANISM: Unknown
<220> FEATURE:
<223> OTHER INFORMATION: Description of Unknown Organism:human clathrin

<400> SEQUENCE: 18
acccaggagc cugagagcau c                                              21

<210> SEQ ID NO 19
<211> LENGTH: 21
<212> TYPE: RNA
<213> ORGANISM: Unknown
<220> FEATURE:
<223> OTHER INFORMATION: Description of Unknown Organism:  rat KCC1

<400> SEQUENCE: 19
cccaaggagc caaggagcac g                                              21

<210> SEQ ID NO 20
<211> LENGTH: 21
<212> TYPE: RNA
<213> ORGANISM: Unknown
<220> FEATURE:
<223> OTHER INFORMATION: Description of Unknown Organism:  mouse PKC
      alpha

<400> SEQUENCE: 20
gccagcgagc cagagagccg g                                              21

<210> SEQ ID NO 21
<211> LENGTH: 21
<212> TYPE: RNA
<213> ORGANISM: Unknown
<220> FEATURE:
<223> OTHER INFORMATION: Description of Unknown Organism:  human
      chromogranin

<400> SEQUENCE: 21
gaccaggagc uggagagccu g                                              21

<210> SEQ ID NO 22
<211> LENGTH: 21
<212> TYPE: RNA
<213> ORGANISM: Unknown
<220> FEATURE:
<223> OTHER INFORMATION: Description of Unknown Organism:  human
      phosphorylase <400> SEQUENCE: 22
cccaaggagc cagacugcuu c                                              21

<210> SEQ ID NO 23
<211> LENGTH: 21
<212> TYPE: RNA
<213> ORGANISM: Unknown
<220> FEATURE:
<223> OTHER INFORMATION: Description of Unknown Organism:  mouse
      cyritestin

<400> SEQUENCE: 23
gccaaggagg cagagacaca a                                              21

<210> SEQ ID NO 24
<211> LENGTH: 21
<212> TYPE: RNA
<213> ORGANISM: Unknown
<220> FEATURE:
<223> OTHER INFORMATION: Description of Unknown Organism:  mouse HBP44
```

```
<400> SEQUENCE: 24
ucccuagagc cagagcgcau g                                              21

<210> SEQ ID NO 25
<211> LENGTH: 21
<212> TYPE: RNA
<213> ORGANISM: Unknown
<220> FEATURE:
<223> OTHER INFORMATION: Description of Unknown Organism:  human LIMK

<400> SEQUENCE: 25
cccauggagc cagagaguga g                                              21

<210> SEQ ID NO 26
<211> LENGTH: 21
<212> TYPE: RNA
<213> ORGANISM: Unknown
<220> FEATURE:
<223> OTHER INFORMATION: Description of Unknown Organism:  human IGFR1

<400> SEQUENCE: 26
gaccuggagc cagagaacau g                                              21

<210> SEQ ID NO 27
<211> LENGTH: 21
<212> TYPE: RNA
<213> ORGANISM: Unknown
<220> FEATURE:
<223> OTHER INFORMATION: Description of Unknown Organism:  mouse FLI-2

<400> SEQUENCE: 27
cccaaggagc cagaacagcu g                                              21

<210> SEQ ID NO 28
<211> LENGTH: 21
<212> TYPE: RNA
<213> ORGANISM: Unknown
<220> FEATURE:
<223> OTHER INFORMATION: Description of Unknown Organism:  HIV-2 tat,vpr

<400> SEQUENCE: 28
uugaaggagc cagagagcuc a                                              21

<210> SEQ ID NO 29
<211> LENGTH: 21
<212> TYPE: RNA
<213> ORGANISM: Unknown
<220> FEATURE:
<223> OTHER INFORMATION: Description of Unknown Organism:
      hepatitisC NS-5

<400> SEQUENCE: 29 gcaaggggc cagagagcau c                                               21

<210> SEQ ID NO 30
<211> LENGTH: 7
<212> TYPE: PRT
<213> ORGANISM: Unknown
<220> FEATURE:
<223> OTHER INFORMATION: Description of Unknown Organism:  MBP consensus

<400> SEQUENCE: 30

Ala Lys Glu Pro Glu Ser Met
 1               5
```

MYELIN BASIC PROTEIN MRNA TRANSPORT AND TRANSLATION ENHANCER SEQUENCES

This invention was made with United States government support under grant NIH-NS-15190 awarded by the National Institute of Health. The United States government has certain rights in the invention.

BACKGROUND OF THE INVENTION

Newly synthesized mRNA which is exported from the nucleus is subject to a variety of competing macromolecular interactions. The 5' cap and poly(A) tail are substrates for binding by cap binding protein and poly(A)-binding protein, respectively. The mRNA is also competent for interaction with the translational machinery by formation of the initiation complex, which includes ribosome subunit binding (Hershey, J. W. B., 1991, Ann. Rev. Biochem. 60:717–55). Interactions which are inhibitory to translation can also occur masking the mRNA and creating a nontranslated pool of messages (Curtis, D., et al., 1995, Cell, 81:171–178; Vasalli, J. D., et al., 1989, Genes & Devel., 3:2163–2171; Richter, J. D., 1991, Bioessays, 13(4):179–183). Some mRNAs are transported and localized to specific subcellular sites, which must involve association with a transport machinery while the mRNA is in transit. Localization of mRNA may also involve interaction with immobile components of the cell in order to anchor the mRNA at the correct destination. mRNAs are also subject to degradation which must involve recognition by degradation enzymes (Pelz, S. W., et al., 1992, Curr. Opin. Cell Biol., 14:979–983; Sachs, A., 1993, Cell, 74(3):413–421). An mRNA, therefore, represents a substrate for many interactions which determine its subcellular location, concentration, and level of expression. Presumably, there are discrete elements within the mRNA that mediate each of these various interactions.

The first suggestion of spatial localization of specific mRNAs within cells came from studies of myelin and myelin basic protein (MBP) mRNA (Colman, D. R., et al., 1982, J. Cell Biol., 95:598–608). Detection of MBP mRNA in a highly purified myelin fraction was the basis for later research that showed the localization of MBP mRNA to the peripheral myelin membranes of oligodendrocytes in vivo (Kristensson, K., et al., 1986, Nature (Lond.), 322:544–547; Verity, N. A., et al., 1988, J. Neurosci. Res., 21:238–248) and in vitro (Holmes, E., et al., 1988, J. Neurosci. Res., 19:389–396; Shiota, C., et al., 1989, Dev. Brain Res., 45:83–94; Barbarese, E., 1991, J. Neurosci. Res., 29:271–281). In retrospect, previous work on targeting of mRNA for secretory and membrane proteins to the rough endoplasmic reticulum (ER) by the nascent polypeptide chain also implicitly describes a localization of mRNA to a subcellular site (Blobel, G., et al., 1975, J. Cell Biol., 67:835–851).

Recently, evidence for the localization of mRNAs to subdomains within the rough ER has been reviewed (Okita, T. W., et al., 1994, Trends Cell Biol., 4:91–96). Functional consequences of RNA localization have been demonstrated in Drosophila. Proper localization of Drosophila bicoid and nanos mRNA is required for establishment of the anterior/posterior axis of the embryo (St. Johnston, D., et al., 1992, Cell, 68(2):201–219). Many RNAs are also localized during creation of the dorsal/ventral axis in Xenopus oocytes (Melton, D. A., et al., 1989, In Ciba Foundation Symposium, Cellular Basis of Morphogenesis, 144:16–30). In addition, motile fibroblasts (Singer, R. H., et al., 1989, J. Cell Biol., 108(6):2343–2353), and terminally differentiated neurons localize specific messages (Garner, C. C., et al., 1988, Nature (Lond.), 336:674–677; Bruckenstein, D. A., et al., 1990, Neuron, 5:809–819; Kleiman, R., et al., 1990, Neuron, 5:821–830). The localization of mRNAs has been extensively reviewed (Steward, O., et al., 1992, Trends Neurosci, 15(5):180–186; Wilhelm, J. E., et al., 1993, J. Cell Biol., 123(2):269–274; St. Johnston, D., 1995, Cell, 81:161–170).

All the currently described cis-acting signals for RNA localization reside in the 3'UTR of the mRNA. Cis-acting signals have been defined for the localization of bicoid (Macdonald, P. M., et al., 1988, Nature (Lond.), 336:595–598; Macdonald, P. M., et al., 1993, Development, 118:1233–1243), nanos (Wharton, R. P., et al., 1991, Cell, 67:955–967; Gavis, E. R., et al., 1992, Cell, 71:301–313), oskar (Ephrussi, A. L., et al., 1992, Nature (Lond.), 358:387–392; Kim-Ha, J., et al., 1993, Development, 119 (1):169–178), Vg1 (Mowry, K. L., et al., 1992, Science (Wash. D.C.), 255(5047):991–994), β-actin (Kislauskis, E. H., et al., 1994, J. Cell Biol., 127–1441–451), cyclin B (Dalby, B., et al., 1993, EMBO (Eur. Mol. Biol. Organ.) J., 12(3):1219–1227), K10 (Cheung, H. K., et al., 1992, Development, 114(3):653–661), and even-skipped (Davis, I., et al., 1991, Cell, 67:927–940) mRNAs. There are two examples of mRNA localization in Drosophila where multiple RNA elements have been described that control different steps in a multi-step pathway. The localization of oskar to the posterior pole of Drosphila oocytes occurs in several steps (Kim-Ha, J., et al., 1993, Development, 119(1):169–178). The oskar mRNA first moves from the nurse cells into the oocyte and accumulates at the anterior margin. The final step in oskar mRNA localization is movement to the posterior pole. Recently, the previously defined bicoid element (Macdonald, P. M., et al., 1988, Nature (Lond.), 336:595–598) has been subdivided into independent elements which control different steps in the localization pathway (Macdonald, P. M., et al., 1993, Development, 118:1233–1243).

Previous work has shown that MBP mRNA microinjected into oligodendrocytes is assembled into RNA granules that are transported along the processes and localized to the myelin compartment while control mRNAs (globin and actin) are assembled into RNA granules that remain in the perikaryon (Ainger et al., 1993). The different distribution of these mRNAs is presumably controlled by some aspect of their structure.

A multi-step pathway for MBP mRNA localization in oligodendrocytes has been proposed (Ainger, K., et al., 1993, J. Cell Biol., 123(2):431–441). The pathway includes: assembly of the RNA into granules in the perikaryon, anterograde transport along cellular processes and localization within the myelin compartment. Granule assembly, transport, and localization occur in spatially distinct subcellular compartments (the perikaryon, processes, and myelin compartment, respectively). Specific nucleotide sequences responsible for localization and transport remained unknown prior to the present invention.

The present invention provides sequences isolated from the 3'UTR of MBP which direct transport, localization and increase translational efficiency of native (i.e., MBP) and heterologous mRNA transcripts when present in such transcripts.

BRIEF DESCRIPTION OF THE DRAWINGS

The file of this patent contains at least one drawing executed in color as determined by the U.S. Patent and Trademark Office. Copies of this patent with color drawing(s) will be provided by the Patent and Trademark Office upon request and payment of the necessary fees.

FIG. 3 (upper portion) shows homologies among different MBP MRNA RTSs and transported mRNAS with RTS homologies. The lower portion for the figure shows RTS homologies in other mRNAs. All sequences are from mature RNAs. The sequence source and location for the RTS homology is indicated. Highlighted bases represent the consensus, defined as 13 or more matches out of 20. Single letter amino acid code of the consensus reading frame is shown below the consensus. The number of matches in protamine 2 mRNA and MAP 2A can be increased by shifting the mismatched segments 1 base to the left.

FIG. 13A is a photomicrograph showing oligodendrocytes microinjected with PLP-RTS RNA (FIG. 12, transcript N) immunofluorescently labeled with anti-digoxigenin antibodies.

FIG. 13B is a photograph showing oligodendrocytes microinjected with PLP-RTS RNA (FIG. 12, transcript N) immunofluorescently labeled with anti-BIP antibodies.

FIG. 13C is a photomicrograph showing PLP RNA (FIG. 11, transcript M), immunofluorescently labeled with anti-digoxigenin.

FIG. 13D is a photomicrograph showing PLP RNA (FIG. 11, transcript M), immunofluorescently labeled with anti-BIP antibodies.

SUMMARY OF THE INVENTION

Figure 1:
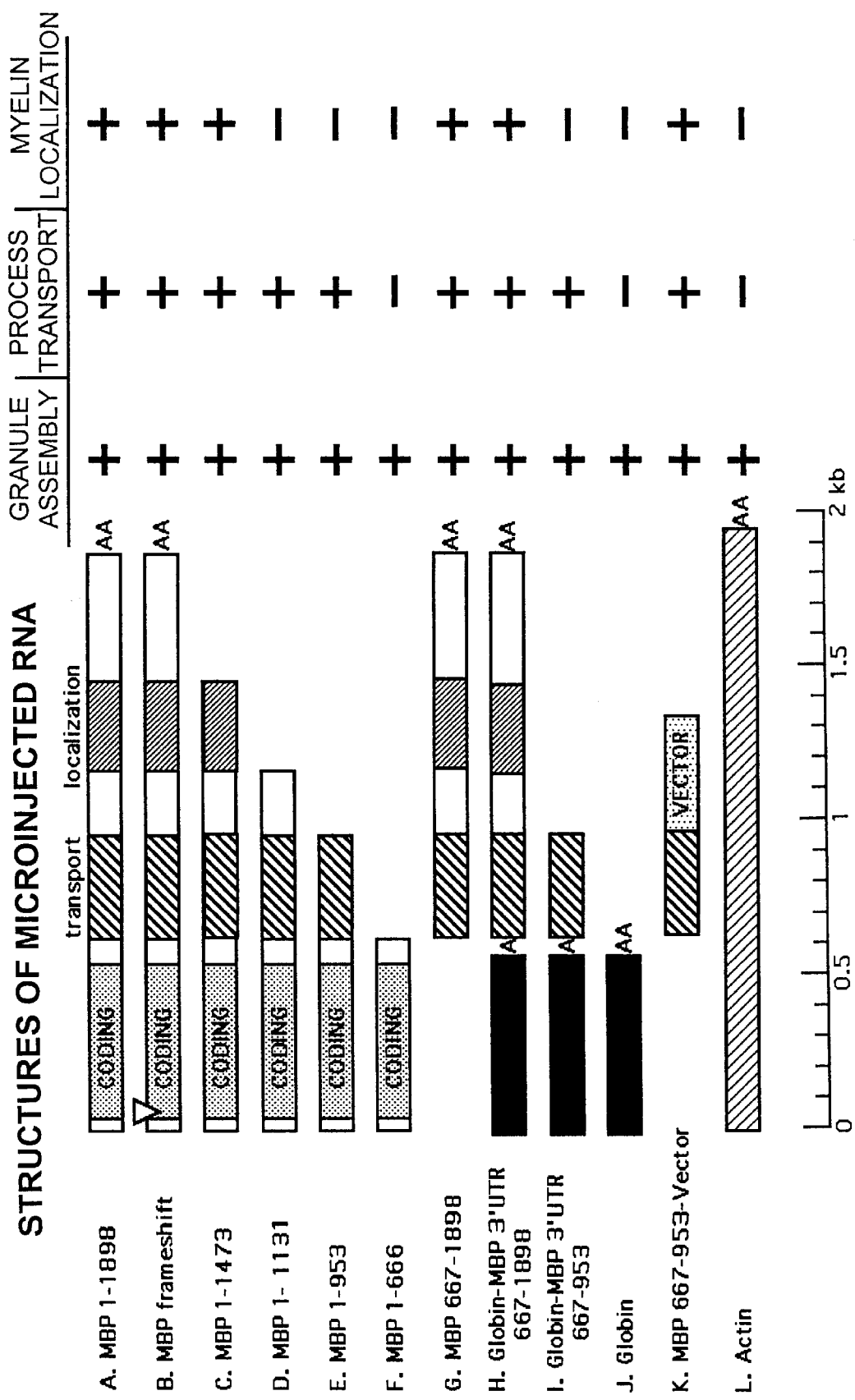
FIG. 1 depicts the structures of various myelin basic protein (MBP) RNA transcripts made from templates containing coding sequence and 3' untranslated regions (A–H). Globin and actin transcripts are also depicted (I–K). A: full length MBP, B: frame shifted full length MBP, C: EcoRI truncated MBP, D: BstEII truncated MBP, E: PvuII truncated MBP, F: SalI truncated MBP, G: SalI fragment of MBP 3' UTR, H: SalI-PvuII fragment of MBP 3' UTR, I: Chimeric construct of X. laevis β-globin with SalI fragment of MBP 3' UTR, J: X. laevis β-globin, K. Mouse β-actin. Plus (+) indicates mRNA distribution was observed in the majority of several hundred injected cells for each of the transcripts A–K.

The present invention provides isolated nucleic acid molecules which comprise sequences from the 3' UTR of myelin basic protein (MBP) mRNA. The subject isolated nucleic acid molecules confer properties such as localization, transport and increased translational efficiency of a heterologous mRNA transcript when transcribed into such mRNA.

In one embodiment of the invention, there is provided an isolated nucleic acid molecule comprising a cis-acting mRNA transport sequence (RTS) derived from the 3'-untranslated region of myelin basic protein (MBP) mRNA and corresponding to nucleotides 667 to 953 of an MBP cDNA or a portion thereof wherein said nucleic acid molecule enhances transport of a heterologous mRNA transcript when transcribed into said transcript.

In another embodiment of the invention, there is provided an isolated nucleic acid molecule comprising a cis-acting mRNA localization enhancer (RLE) derived from the 3'-untranslated region of myelin basic protein (MBP) mRNA and corresponding to nucleotides 1130 to 1473 of an MBP cDNA or a portion thereof wherein said nucleic acid molecule enhances localization of a heterologous mRNA transcript when transcribed into said transcript.

In a preferred embodiment, an isolated nucleic acid molecule is provided which comprises a cis-acting RNA transport sequence (RTS) derived from the 3' untranslated region of rat or mouse myelin basic protein (MBP) mRNA having the sequence set forth in SEQ ID NO:3.

In another preferred embodiment, an isolated nucleic acid molecule is provided which comprises a cis-acting RNA transport sequence (RTS) derived from the 3' untranslated region of a human myelin basic protein (MBP) mRNA having the sequence set forth in SEQ ID NO:4.

In another preferred embodiment, there is provided an isolated nucleic acid molecule comprising a cis-acting RNA transport sequence (RTS) derived from the 3' untranslated region of a human myelin basic protein (MBP) mRNA having the sequence set forth in SEQ ID NO:5.

The present invention contemplates isolated nucleic acid molecules having those sequences set forth in SEQ ID NOs:3, 4 and 5 which also have contained therein at least one insertion, deletion, or substitution of one or more nucleotides and wherein the property of enhancement of translational efficiency and transport of a heterologous mRNA transcript when transcribed into said transcript is maintained by the isolated nucleic acid molecules.

The present invention also provides vectors comprising the subject RTS or RLE sequences. In one embodiment, the vectors comprise at least one RTS derived from the 3'-untranslated region of myelin basic protein (MBP) mRNA and corresponding to nucleotides 667 to 953 of an MBP cDNA or a portion thereof wherein said nucleic acid molecule enhances transport of a heterologous mRNA transcript when transcribed into said transcript.

In another embodiment, the vectors comprise at least one cis-acting mRNA localization enhancer (RLE) derived from the 3'-untranslated region of myelin basic protein (MBP) mRNA and corresponding to nucleotides 1130 to 1473 of an MBP cDNA or a portion thereof wherein said nucleic acid molecule enhances localization of a heterologous mRNA transcript when transcribed into said transcript.

In yet another embodiment of the invention, the vectors comprise at least one isolated nucleic acid corresponding to an RTS derived from the 3' untranslated region of myelin basic protein (MBP) mRNA and having the sequence set forth in SEQ ID NO:3 or an isolated nucleic acid molecule having at least one of an insertion, deletion, or substitution of one or more nucleotides wherein said isolated nucleic acid molecule enhances translational efficiency of a heterologous mRNA transcript when transcribed into said transcript.

In yet another aspect of the invention, the vectors comprise at least one isolated nucleic acid corresponding to an RTS derived from the 3' untranslated region of myelin basic protein (MBP) mRNA and having the sequence set forth in SEQ ID NO:4 or an isolated nucleic acid molecule having at least one of an insertion, deletion, or substitution of one or more nucleotides wherein said isolated nucleic acid molecule enhances translational efficiency of a heterologous mRNA transcript when transcribed into said transcript.

In yet another aspect of the invention, the vectors comprise at least one isolated nucleic acid corresponding to an RTS derived from the 3' untranslated region of myelin basic protein (MBP) mRNA and having the sequence set forth in SEQ ID NO:5 or an isolated nucleic acid molecule having at least one of an insertion, deletion, or substitution of one or more nucleotides wherein said isolated nucleic acid molecule enhances translational efficiency of a heterologous mRNA transcript when transcribed into said transcript.

In another aspect of the present invention, there are provided methods for increasing translation of a heterologous gene. The method comprises transforming a eukaryotic cell with at least one of the subject vectors having coding sequence for a heterologous gene.

In another aspect of the present invention, there is provided a method of gene therapy comprising isolating target cells from a patient in need of said gene therapy, infecting said target cells with an expression vector comprising coding sequence for a heterologous protein operably linked to a 5' regulatory region and a 3' termination sequence in addition to viral sequences required for packaging, reverse transcription, and integration into a host genome wherein sequence for at least one subject RTS is inserted in the expression vector in at least one position 5' or 3' to the coding sequence for the heterologous protein and; reintroducing the target cells into the patient.

Preferably, the gene therapy method comprises administering to a patient in need of said gene therapy, a therapeutically effective amount of virions produced by a helper cell transfected with a viral vector comprising coding sequence for a heterologous protein operably linked to a 5' regulatory region and a 3' termination sequence in addition to retroviral sequences required for packaging, reverse transcription, and integration into a host genome wherein sequence for at least one subject RTS is inserted in the expression vector in at least one position 5' or 3' to the coding sequence for the heterologous protein.

DETAILED DESCRIPTION OF THE INVENTION

The present invention provides isolated nucleic acid molecules which comprise sequences from the 3' UTR of myelin basic protein (MBP) mRNA. The subject isolated nucleic acid molecules confer properties such as localization, transport and increased translational efficiency of a heterologous mRNA when transcribed into said mRNA.

In one embodiment of the invention, there is provided an isolated nucleic acid molecule comprising a cis-acting mRNA transport sequence (RTS) derived from the 3'-untranslated region of myelin basic protein (MBP) mRNA and corresponding to nucleotides 667 to 953 of an MBP cDNA or a portion thereof wherein said nucleic acid molecule enhances transport of a heterologous mRNA transcript when transcribed into said transcript.

In another embodiment of the invention, there is provided an isolated nucleic acid molecule comprising a cis-acting mRNA localization enhancer (RLE)derived from the 3'-untranslated region of myelin basic protein (MBP) mRNA and corresponding to nucleotides 1130 to 1473 of an MBP cDNA or a portion thereof wherein said nucleic acid molecule enhances localization of a heterologous mRNA transcript when transcribed into said transcript.

By "heterologous transcript" is meant an RNA transcript other than an MBP mRNA transcript. The isolated nucleic acids of the present invention also function when used to enhance transport of the native MBP mRNA transcript when transcribed into said transcript.

In a preferred embodiment, an isolated nucleic acid molecule is provided which comprises a cis-acting RNA transport sequence (RTS) derived from the 3' untranslated region of rat or mouse myelin basic protein (MBP) mRNA having the sequence set forth in SEQ ID NO:3.

In another preferred embodiment, an isolated nucleic acid molecule is provided which comprises a cis-acting RNA transport sequence (RTS) derived from the 3' untranslated region of a human myelin basic protein (MBP) mRNA having the sequence set forth in SEQ ID NO:4.

In another preferred embodiment, there is provided an isolated nucleic acid molecule comprising a cis-acting RNA transport sequence (RTS) derived from the 3' untranslated region of a human myelin basic protein (MBP) mRNA having the sequence set forth in SEQ ID NO:5.

The present invention contemplates isolated nucleic acid molecules having those sequences set forth in SEQ ID NOs:3, 4 and 5 which also have contained therein at least one insertion, deletion, or substitution of one or more nucleotides and wherein the property of enhancement of translational efficiency and transport of a heterologous mRNA transcript when transcribed into said transcript is maintained by the isolated nucleic acid molecules.

Figure 3:
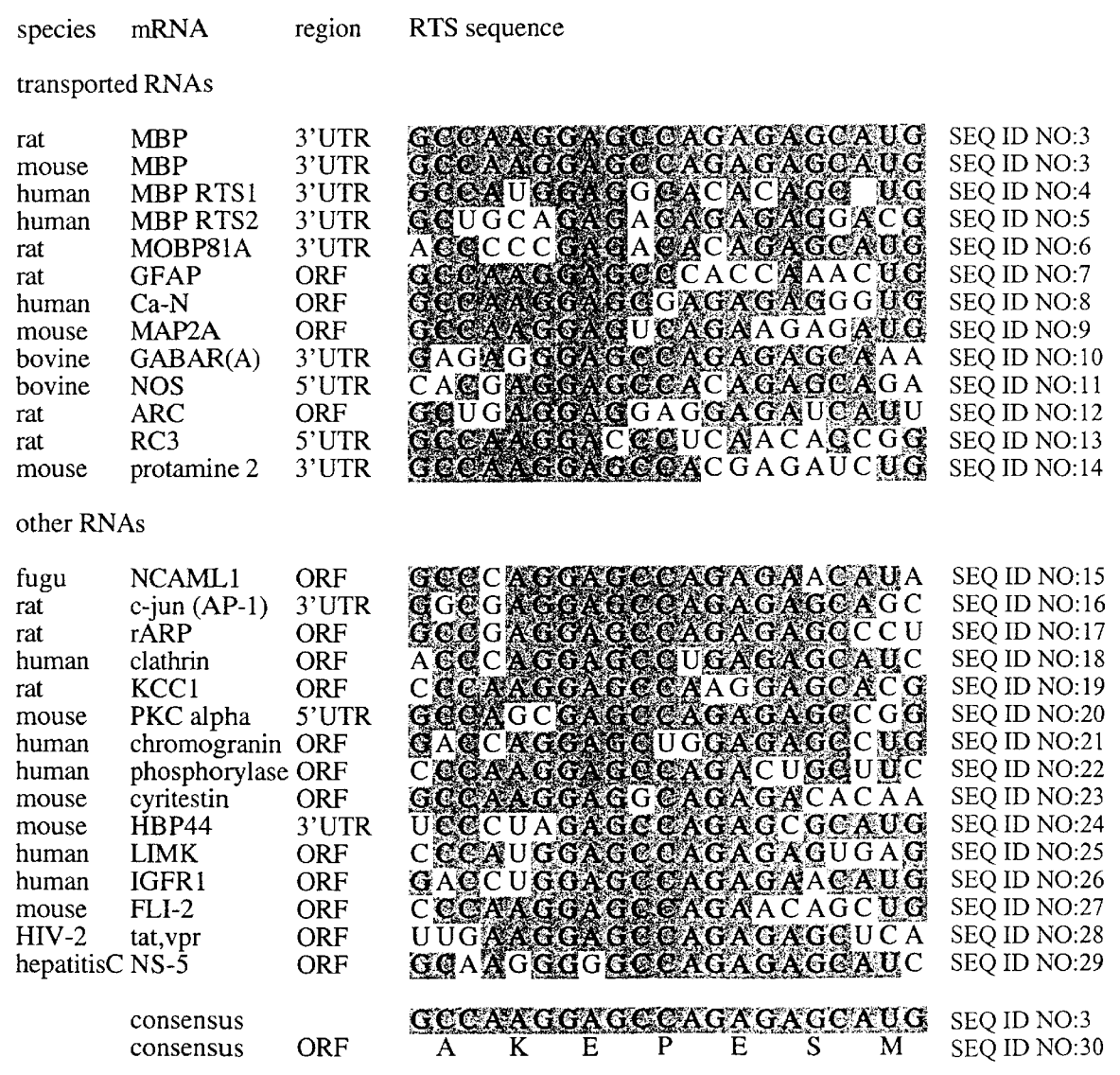

Examples of 21 nt long RTSs having specific nucleotide substitutions introduced into the sequences as set forth in SEQ ID NOs: 3–5 are listed in FIG. 3. RTSs comprising these sequences, i.e., SEQ ID NOs: 6–29 are specifically contemplated by the present invention.

The isolated nucleic acid molecules of the present invention can be produced by restriction of a myelin basic protein cDNA or genomic DNA molecule. For example, portions of the 3' UTR of an MBP cDNA or genomic clone may be used in order to isolate the subject nucleic acid molecules of the present invention. The nucleotide sequence of a cDNA coding for rat MBP may be found in Roach et al., 1983 *Cell* 34:799–806. The 3'UTR of rat MBP may be subcloned as a SalI/HindIII fragment or a SalI/PvuII fragment. In order to isolate the RTS having nucleotides 667–953 or the RLE having nucleotides 1130–1473 further digestion of the 3' UTR may be necessary. The isolated nucleic acid molecules of the present invention may be generated by larger nucleic acid fragments having excess sequence on either or both 3' and 5' ends removed via exonuclease III-mediated deletion. This is accomplished by digesting appropriately prepared DNA with exonuclease III (exoIII) and removing aliquots at increasing intervals of time during the digestion. The resulting successively smaller fragments of DNA may be sequenced to determine the exact endpoint of the deletions. There are several commercially available systems which use exonuclease III (exoIII) to create such a deletion series, e.g. Promega Biotech, "Erase-A-Base" system. Alternatively, PCR primers can be defined to allow direct amplification of the subject nucleic acid fragments.

In addition, the present invention contemplates an RTS corresponding to a portion of nucleotides 667 to 953 of an MBP cDNA, as well as an RLE corresponding to a portion of nucleotides 1130 to 1473 of an MBP cDNA. The skilled artisan is aware of methods for removing portions of the subject defined nucleic acid fragments e.g., using exonuclease III-mediated deletion as described above.

Using the same methodologies, the ordinarily skilled artisan can generate one or more deletion fragments of nucleotides 667–953 or 1130 to 1473 of an MBP cDNA which retain the capacity to enhance translational efficiency or direct transport or localization of an mRNA transcript.

The identification of sequences which enhance transport and localization of isolated nucleic acid fragments corresponding to MBP cDNA sequences such as nucleotides 667–953 and portions thereof, nucleotides 1130–1473 and portions thereof, as well as sequences such as SEQ ID NOs:3, 4, and 5 and modifications thereto such as insertions, substitutions or deletions of one or more nucleotides can be accomplished by transcriptional fusions of specific sequences within the MBP 3' UTR with the coding sequence of a heterologous gene, transfer of the chimeric gene into an appropriate host, and detection of the expression of resulting mRNA transcripts.

The method used to detect the effect on expression by an RTS or RLE sequence depends upon whether RNA transport or translational efficiency is to be assayed. For example, if the effect on transport of an RNA transcript is to be assayed, then vectors comprising RNA transcription templates are first constructed. The RNA transcription template comprises a an RTS or RLE sequence and a portion of the native MBP gene or a heterologous gene. The native MBP gene or heterologous gene is under the control of a promoter which functions in eukaryotic cells. After transcription, the mRNA transcripts are microinjected into cells and the cells examined by microscopy to assay for transport. It is desirable to prepare capped mRNA transcripts which can be accomplished by adding 7-methyl guanosine cap during the transcription reaction. Preferably, RNA is labeled by addition of digoxigenin-UTP or other immunofluorescence labeled nucleotide so that the RNA transcripts may be visualized in a cell. Antibodies to the labeled RNA such as anti-digoxigenin may also be used.

If the effect on translation of an RNA transcript is to be assayed, then an in vivo translation assay may be performed after microinjection of RNA transcripts made from the RNA transcription template constructs discussed above. Preferably, the heterologous gene in the template construct is a reporter gene which can be assayed for translation. For example, the coding sequence for green fluorescent protein (GFP) from *Aequorea Victoria* may be used as a reporter for translation. Coding sequence for firefly luciferase may also be used. Microinjected cells showing increased fluorescence when compared to control cells are indicative of increased translational efficiency.

The subject nucleic acid molecules and oligonucleotides of the present invention can be made by any of a myriad of procedures known for making DNA or RNA oligonucleotides. For example, such procedures include enzymatic synthesis and chemical synthesis.

Enzymatic methods of DNA oligonucleotides synthesis frequently employ Klenow, T7, T4, Taq or *E. coli* DNA polymerase as described in Sambrook et al. 1989, in *Molecular Cloning: A Laboratory Manual*, Cold Spring Harbor, N.Y. Enzymatic methods of RNA oligonucleotide synthesis frequently employ SP6, T3 or T7 RNA polymerase as described in Sambrook et al., 1989. Reverse transcriptase can also be used to synthesize DNA from RNA (Sambrook et al. 1989). To prepare oligonucleotides enzymatically requires a template nucleic acid which can either be synthesized chemically, or be obtained as mRNA, genomic DNA, cloned genomic DNA, cloned cDNA or other recombinant DNA. Some enzymatic methods of DNA oligonucleotide synthesis can require an additional primer oligonucleotide which can be synthesized chemically. Finally linear oligonucleotides can be prepared by polymerase chain reaction (PCR) techniques as described, for example, by Saiki et al., 1988, *Science* 239: 487.

Chemical synthesis of linear oligonucleotides is well known in the art and can be achieved by solution or solid phase techniques. Moreover, linear oligonucleotides of defined sequence can be purchased commercially or can be made by any of several different synthetic procedures including the phosphoramidite, phosphite triester, H-phosphonate and phosphotriester methods, typically by automated synthesis methods. The synthesis method selected can depend on the length of the desired oligonucleotide and such choice is within the skill of the ordinary artisan. For example, the phosphoramidite and phosphite triester method produce oligonucleotides having 175 or more nucleotides while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann, et al. (1990, *Chemical Reviews* 90: 543–584) provide references and outline procedures for making oligonucleotides with modified bases and modified phosphodiester linkages.

The subject isolated nucleic acid molecules and oligonucleotides may be purified by polyacrylamide gel electrophoresis, or by any of a number of chromatographic methods, including gel chromatography and high pressure liquid chromatography. To confirm a nucleotide sequence, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104: 976; Viari, et al., 1987, *Biomed. Enciron. Mass Spectrom.* 14: 83; Grotjahn et al., 1982, *Nuc. Acid Res.* 10: 4671). Sequencing methods are also available for RNA oligonucleotides.

The present invention also provides vectors comprising the subject RTS or RLE sequences. For example, the vectors may comprise at least one RTS derived from the 3'-untranslated region of myelin basic protein (MBP) mRNA and corresponding to nucleotides 667 to 953 of an MBP cDNA or a portion thereof wherein said nucleic acid molecule enhances transport of a heterologous mRNA transcript when transcribed into said transcript.

In another aspect of the invention, the vectors comprise at least one cis-acting mRNA localization enhancer (RLE) derived from the 3'-untranslated region of myelin basic protein (MBP) mRNA and corresponding to nucleotides 1130 to 1473 of an MBP cDNA or a portion thereof wherein said nucleic acid molecule enhances localization of a heterologous mRNA transcript when transcribed into said transcript.

In yet another aspect of the invention, the vectors comprise at least one isolated nucleic acid corresponding to an RTS derived from the 3' untranslated region of myelin basic protein (MBP) mRNA having the sequence set forth in SEQ ID NO:3 or an isolated nucleic acid molecule having at least one of an insertion, deletion, or substitution of one or more nucleotides wherein said isolated nucleic acid molecule enhances translational efficiency and transport of a heterologous mRNA transcript when transcribed into said transcript.

In yet another aspect of the invention, the vectors comprise at least one isolated nucleic acid corresponding to an RTS derived from the 3' untranslated region of myelin basic protein (MBP) mRNA having the sequence set forth in SEQ ID NO:4 or an isolated nucleic acid molecule having at least one of an insertion, deletion, or substitution of one or more nucleotides wherein said isolated nucleic acid molecule enhances translational efficiency and transport of a heterologous mRNA transcript when transcribed into said transcript.

In yet another aspect of the invention, the vectors comprise at least one isolated nucleic acid corresponding to an RTS derived from the 3' untranslated region of myelin basic protein (MBP) mRNA having the sequence set forth in SEQ ID NO:5 or an isolated nucleic acid molecule having at least one of an insertion, deletion, or substitution of one or more nucleotides wherein said isolated nucleic acid molecule enhances translational efficiency and transport of a heterologous mRNA transcript when transcribed into said transcript. In these embodiments, the RTS may be placed at a position upstream or downstream from the multiple cloning site. The position of the RTS will be maintained upon cloning other nucleic acid fragments into the multiple cloning site.

Other embodiments include vectors such as any of those described above and which further comprise coding sequence for a heterologous gene operably linked to a 5' regulatory region and a 3' transcription termination sequence. In these embodiments, the RTS may be placed downstream from the 5' regulatory region or upstream from the 3' termination sequence.

Similar vectors comprising one or more RTS sequences as set forth in any of SEQ ID NOs: 6–29 are also contemplated by the present invention.

The vectors of the present invention can be constructed by standard techniques known to one of ordinary skill in the art and found, for example, in Sambrook et al. (1989) in *Molecular Cloning: A Laboratory Manual*, or any of a myriad of laboratory manuals on recombinant DNA technology that are widely available. A variety of strategies are available for ligating fragments of DNA, the choice of which depends on the nature of the termini of the DNA fragments and can be readily determined by the skilled artisan.

The vectors of the present invention may also contain other sequence elements to facilitate vector propagation, isolation and subcloning; for example, selectable marker genes and origins of replication that allow for propagation and selection in bacteria and host cells. Selectable marker genes can include ampicillin and tetracycline resistance genes for propagation in bacteria or neomycin or zeocin resistance for selection in mammalian cells. In addition, the vectors of the present invention may comprise a sequence of nucleotides for one or more restriction endonuclease sites. Use of nucleic acid fragments having multiple cloning sites are also contemplated by the present invention as are reporter genes. Coding sequences for heterologous genes, sequences for selectable markers, reporter genes and multiple cloning sites are well known to the skilled artisan. Examples of reporter genes include GFP, luciferase, CAT, and β-galactosidase. By "heterologous genes" is meant coding sequences or parts thereof which are not derived from MBP.

The vectors of the present invention may comprise viral sequences required for packaging, reverse transcription, and integration into a host genome in addition to coding sequence for a biologically active protein and at least one subject RTS. Such vectors are useful for transfecting into helper cells from which recombinant virions can be produced. Virions containing the recombinant are used to transfect target cells.

In another aspect of the present invention, there are provided methods for increasing translation of a heterologous gene. The method comprises transforming a eukaryotic cell with at least one of the subject vectors having coding sequence for a heterologous gene. Levels of translation may be assayed by any number of methods such as, for example, in vivo translation, PAGE, or western blots. Such methods are useful for increasing production of recombinantly produced proteins in vivo on either a small, research scale or on a large commercial scale.

Different types of eukaryotic cells useful for practicing the methods include CHO cells, human fibroblast cells, hematopoietic stem cells, yeast cells and insect cells such as SP9.

Recombinantly produced proteins may comprise any number of structural, therapeutic or biologically active proteins i.e., a polypeptide or protein which affects the cellular mechanism of a cell in which the biologically functional in a number of different cell types. For example, the biologically active protein may be a protein which affects the cellular mechanism of a cell in which the biologically active protein is expressed or to which the biologically active protein is administered. The biologically active protein can also be a protein which improves the health of a mammal by either supplying a missing protein, by providing increased quantities of a protein which is underproduced in the mammal or by providing a protein which inhibits or counteracts an undesired molecule which may be present in the mammal.

The biologically functional protein can be a protein which is essential for normal growth or repair of cells. The biologically functional protein may also be one which is useful in fighting diseases such as cancer, atherosclerosis, sickle-cell anemia and the thalassemias. Examples of such biologically functional proteins are hemoglobin (α,β or γ-globin), hematopoietic growth factors such as granulocyte-macrophage colony stimulating factor (GM-CSF), macrophage colony stimulating factor (M-CSF) and erythropoietin (EPO). Another example is tumor necrosis factor (TNF), which is a molecule that can be used to treat cancer, and in particular, tumors. The tumor suppressor p53 and retinoblastoma (RB) are also contemplated. Various cytokines such as mast cell growth factor (MGF) and interleukins 1–11 are also proteins which are contemplated by the vectors of the present invention.

Thus, any protein which can be produced recombinantly is contemplated for use in the vectors and methods of the present invention. In some instances, the proteins produced by the vectors and methods of the present invention are purified and stored in an appropriate pharmaceutically acceptable carrier for storage and eventual administration to a subject.

Those vectors comprising viral sequences required for packaging, reverse transcription, and integration into a host genome in addition to coding sequence for a biologically active protein and at least one subject RTS are useful in gene therapy methods. The vectors, admixed with a pharmaceutically acceptable carrier, may be administered to a patient following known methods of administration. The vectors may also be used to transfect into helper cells from which recombinant virions can be produced. Virions containing the recombinant virus are used to infect target cells or administer directly to a patient.

Thus, the present invention also provides a method of enhancing gene therapy which comprises administering to a patient in need of said gene therapy, a therapeutically effective amount of an expression vector comprising coding sequence for a heterologous protein operably linked to a 5' regulatory region and a 3' termination sequence in addition to viral sequences required for packaging, reverse transcription, and integration into a host genome wherein sequence for at least one subject RTS is inserted in the expression vector in at least one position 5' or 3' to the coding sequence for the heterologous protein.

Other methods include a method of gene therapy comprising isolating target cells from a patient in need of said gene therapy, infecting said target cells with an expression vector comprising coding sequence for a heterologous protein operably linked to a 5' regulatory region and a 3' termination sequence in addition to viral sequences required for packaging, reverse transcription, and integration into a host genome wherein sequence for at least one subject RTS is inserted in the expression vector in at least one position 5' or 3' to the coding sequence for the heterologous protein and; reintroducing the target cells into the patient.

Preferably, the gene therapy method comprises administering to a patient in need of said gene therapy, a therapeutically effective amount of virions produced by a helper cell transfected with a viral vector comprising coding sequence for a heterologous protein operably linked to a 5' regulatory region and a 3' termination sequence in addition to viral sequences required for packaging, reverse transcription, and integration into a host genome wherein sequence for at least one subject RTS is inserted in the expression vector in at at least one position 5' or 3' to the coding sequence for the heterologous protein.

The invention is further illustrated by the following specific examples which are not intended in any way to limit the scope of the invention.

EXAMPLE 1

Construction of MBP Templates and In Vitro Transcription

Cell Cultures and Reagents

Mouse oligodendrocytes were isolated from mixed primary brain cell cultures and grown as previously described (Ainger et al., 1993). Restriction enzymes and RNA polymerases were obtained from New England BioLabs (Beverly, Mass.), Promega (Madison, Wis.) and Stratagene (La Jolla, Calif.). RNasin and transcription buffers were from Promega. RNA molecular weight markers were from Gibco BRL (Gaithersburg, Md.). Diethylpyrocarbonate (DEPC), mineral oil, and ammonium sulfate were from Sigma (St. Louis, Mo.).

In Vitro Transcription

Transcription templates were prepared from a plasmid containing coding sequence for rat 14K MBP (Roach et al., 1983, Cell 34:799–806) originally subcloned into a pSP64 poly A vector (Promega). Transcription reactions were carried out according to the pSPG64 polyA vector manufacturer's instructions. Digestion with EcoRI and transcription with SP6 polymerase gave an RNA with the first 1473 bases of MBP mRNA. For other truncations the entire MBP cDNA was subcloned into the EcoRI site of pBluescript IISK (Stratagene) to create pKS3. Transcription with T3 polymerase (Promega) resulted in incorporation of a short length of vector-derived sequences from the polylinker on the 5' end of all RNAs. Digestion with SalI, PvuII, and BstEII gave RNAs with the first 666, 953, and 1131 bases, respectively, of rat MBP. HindIII-cut plasmid was used to transcribe full length MBP mRNA containing plasmid-derived polyadenosine and a short 3' sequence from the polylinker. To make RNA with a translational frame shift, the XmaI to HindIII fragment of pKS3 was subcloned into pGEM3 (Promega). The plasmid was linearized with BamHI, filled in with Klenow (New England Biolabs), and religated. The plasmids were grown in dam E. coli and assayed for a newly generated ClaI site. The reading frame shifts to −1 after 13 amino acids of MBP. The polypeptide terminates after an additional 27 out of frame amino acids.

The 3' UTR of MBP was subcloned as a SalI/HindIII fragment into SalI/HindIII cut pGem3. The plasmid was linearized with HindIII and transcribed with T7 polymerase. Similarly, the SalI/PvuII fragment of MBP3' UTR was subcloned into SalI/EcoRV digested pBluescript IISK, digested with PvuII, and transcribed with T7 polymerase. This produced an RNA with a 280 nucleotide (nt) 3' extension of vector-derived sequences. To construct chimeric RNAs, the 3' UTR and the Sal/PvuII fragment of MBP cDNA were subcloned into SalI linearized and SalI/SmaI digested, respectively, Xenopus laevis globin cDNA (D. Melton, Harvard University; pSP64-XβM). A 2 Kb β-actin cDNA was obtained from J. Pachter of University of Connecticut (UCHC). The DNA was digested with EcoRI before transcription. To make RNA, the chimeric plasmids were digested with EcoRV and SmaI, respectively, and transcribed with SP6 polymerase. All RNAs were subjected to electrophoresis in gels containing formaldehyde (Sambrook et al., 1989) to ensure that the injected RNA was a homogeneous population of the appropriate size.

RNA was labeled by addition of digoxigenin-UTP (Boehringer Mannheim) during transcription reactions (Promega) according to manufacturer's instructions. To prepare capped RNA, 7-methyl guanosine cap (Boehringer Mannheim) was added during transcription. The structures of the various transcribed RNAs are depicted in FIG. 1.

EXAMPLE 2

Microinjection Of RNA Transcripts And Intracellular Localization Of Microinjected RNAs The transcribed RNAs of Example 1 (schematically diagramed in FIG. 1)were injected into mouse oligodendrocytes maintained at room temperature for a period of not more than 45 minutes as described previously (Ainger et al., 1993). Several hundred cells were microinjected with each RNA. Distribution patterns as indicated in the right hand portion of FIG. 1 reflect patterns observed in the majority of cells. The results obtained for each RNA were compared with size matched positive and negative controls, microinjected at the same time into cells from the same preparation. Each RNA was assayed in at least three different preparations of oligodendrocytes.

To allow time for transport and localization of the injected RNA, cells were incubated for 15 minutes at 37° C., in medium containing 2% newborn calf serum. This medium also allowed digestion of extracellular RNA that may have leaked into the medium during the injections reducing nonspecific background.

To visualize digoxigenin-labeled RNA, cells were fixed in 4% paraformaldehyde in PBS and incubated with anti-digoxigenin antibodies as previously described (Ainger et al., 1993) or using a mouse monoclonal antidigoxigenin antibody (1:75 dilution), followed by detection with a fluorescein-conjugated goat anti-mouse IgG(Chemicon International). MBP was visualized using rabbit polyclonal anti-MBP followed by Texas Red-conjugated donkey anti-rabbit IgG (Jackson ImmunoResearch). The endoplasmic reticulum (ER) was visualized with rabbit polyclonal anti-BIP and appropriate fluorescent-conjugated secondary antibodies. To visualize fluorescein-labeled RNA in living cells, time lapse images were collected at 10 second intervals as described previously (Ainger et al., 1993).

Laser scanning confocal microscopy was performed with an MRC-600 scanning system (Biorad, Cambridge, MA) mounted on a Zeiss Axioskope (Zeiss, Oberkochen, Germany) equipped with a variety of infinity-corrected high numerical aperture objectives. Results of the microinjection assay indicated a characteristic pattern of distribution in three different compartments of oligodendrocytes: the perikaryon, processes, and myelin compartment. Representative cells illustrating each pattern are shown in FIG. 2. For each RNA template construct, the pattern seen in the majority of cells is indicated in FIG. 1., as "+" or "−".

Figure 2A:
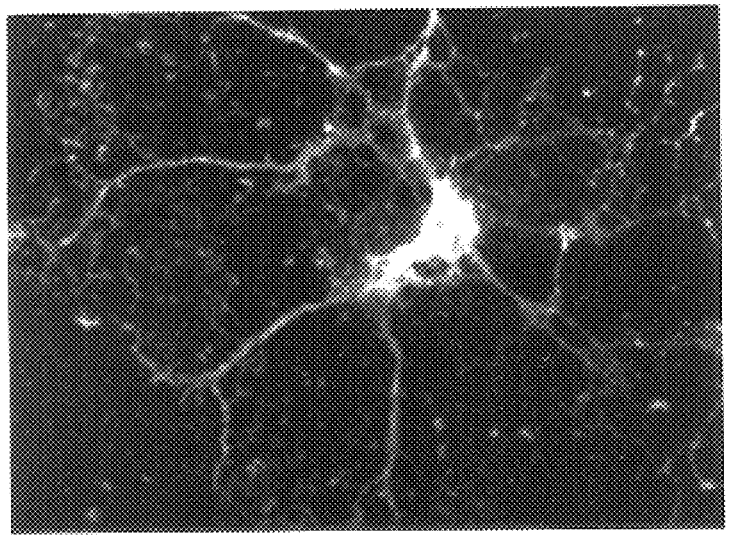
FIG. 2A is a photograph showing a fully transported MBP mRNA as found in granules in the cell body, processes, and membrane sheets representative of constructs A, B, C, G, H, and I.

In the pattern illustrated in FIG. 2A, RNA is found in granules in the cell body, processes, and myelin compartment. Dispersed staining in the myelin compartment is also observed. The presence of RNA granules in the distal processes indicates that RNA is transported in these cells. The presence of granules and dispersed RNA in the myelin compartment indicates that RNA is localized to the peripheral regions of the cell. This distribution pattern was observed with constructs A, B, C, G, H, and I shown in FIG. 1. Taken together, these results define features which are nonessential for transport and localization of MBP mRNA. These features include: the terminal 425 bases of the 3' UTR of MBP mRNA (FIG. 1, transcript C), the first 666 bases of the MBP mRNA including the coding region (FIG. 1, transcript G), and the nascent polypeptide beyond the initial 13 amino acids (FIG. 1, transcript B). The MBP 3' UTR is correctly transported and localized when injected alone (FIG. 1, transcript G) and can confer transport and localization to globin (FIG. 1, transcript I), which is neither transported nor localized when injected (FIG. 1, transcript J). Previously, the 5' cap was shown to have no effect on the transport or localization of microinjected MBP mRNA (Ainger et al., 1993). In addition, the 3' UTR of MBP from 667 to 953 is both necessary and sufficient for specific transport and localization.

Figure 2B:
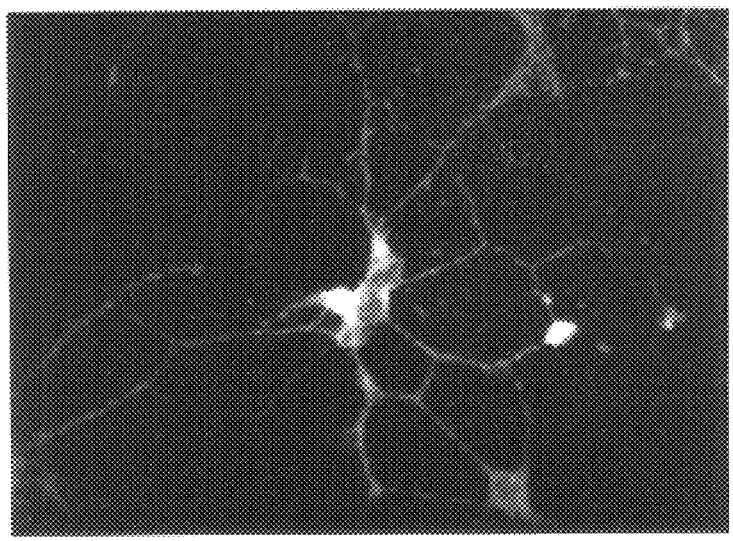
FIG. 2B is a photograph showing mRNA transport to the end of the processes without localization to the membrane sheets, representative of constructs D and E.

In the pattern illustrated in FIG. 2B, RNA is found in granules in the cell body, and in the distal processes, but no granules or dispersed RNA are observed in the peripheral myelin compartment. The presence of RNA granules in the processes indicates that the RNA is transported; the absence of RNA from the myelin compartment indicates that the RNA is not localized to the membrane sheets. This distribution pattern was observed with MBP mRNAs truncated to 953 and 1131 bases (FIG. 1, transcripts D and E). The region from 1131 to 1473, therefore, contains all or part of a signal required for the localization for these RNAs to the myelin compartment.

Figure 2C:
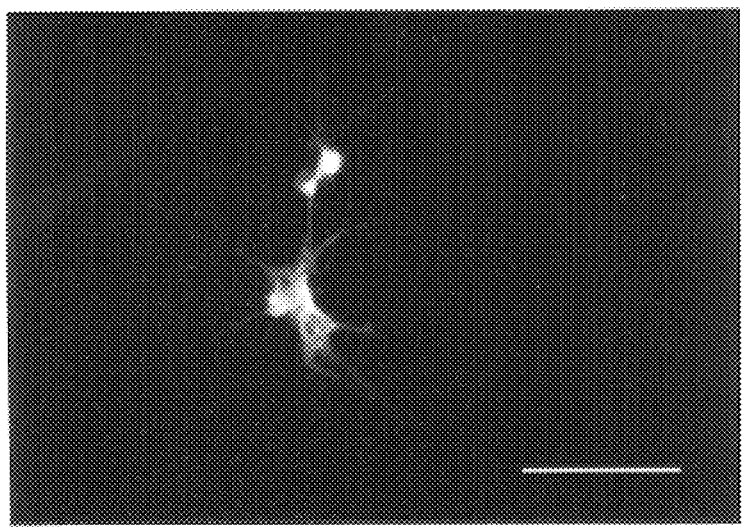
FIG. 2C is a photograph showing non-transported mRNA confined to the perikaryon, representative of constructs F, J, and K. Scale bar represents 25μ.

Microinjection of MBP mRNA truncated to 666 bases (FIG. 1, transcript F) resulted in the pattern shown in FIG. 2C. Granules were present only in the cell body. The absence of granules from the processes indicates that the RNA was not transported; the absence of RNA from the myelin compartment indicates that the RNA was not localized. This pattern was also observed with full length and polyadenylated globin and actin mRNAs (FIG. 1, transcripts J and K). This result demonstrates that the coding region and the first 250 bases of the 3' UTR are not sufficient for any aspect of MBP mRNA transport or localization, although it is sufficient for granule formation. Granule formation is the first step in MBP mRNA localization, although it is not specific to localized mRNAs (Ainger et al., 1993).

Figure 15A:
FIG. 15A is a photomicrograph of an oligodendrocyte injected with transcript A of FIG. 1 and immunofluorescently labeled with anti-digoxigenin antibodies.
Figure 15B:
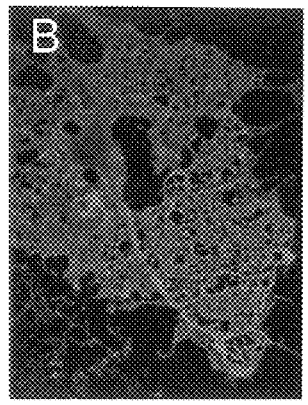
FIG. 15B is a photomicrograph of an oligodendrocyte injected with transcript A of FIG. 1 and immunofluorescently labeled with anti-MBP antibodies.
Figure 15C:
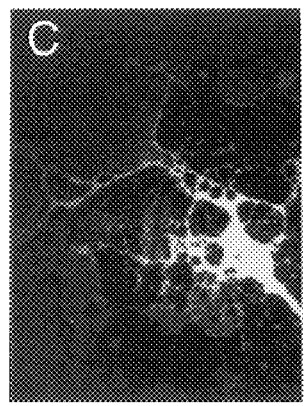
FIG. 15C is a photomicrograph of an oligodendrocyte injected with transcript D of FIG. 1 and immunofluorescently labeled with anti-digoxigenin antibodies.
Figure 15D:
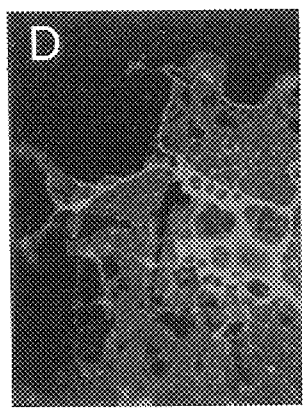
FIG. 15D is a photomicrograph of an oligodendrocyte injected with transcript D of FIG. 1 and immunofluorescently labeled with anti-MBP antibodies.
Figure 15E:
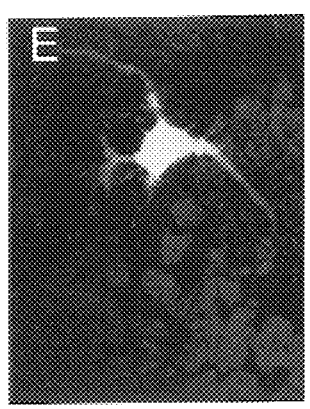
FIG. 15E is a photomicrograph of an oligodendrocyte injected with transcript F of FIG. 1 and immunofluorescently labeled with anti-digoxigenin antibodies.
Figure 15F:
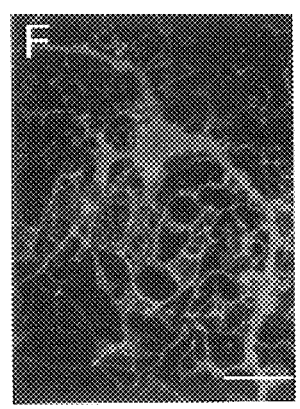
FIG. 15F is a photomicrograph of an oligodendrocyte injected with transcript F of FIG. 1 and immunofluorescently labeled with anti-MBP antibodies.

FIGS. 15A–F also show the results of representative mouse oligodendrocytes microinjected and immunofluorescently labeled with both anti-digoxigenin (FIGS. 15A, 15C and 15E) and anti-MBP antibodies (FIGS. 15B, 15D, and 15F). When full-length, polyadenylated MBP (FIG. 1, transcript A) was injected into oligodendrocytes, granules were observed in the perikaryon, processes, and myelin compartment (FIGS. 15 A and 15B), indicating that this RNA contains signals for granule assembly, transport, and localization, respectively. The distribution pattern was not affected by insertion of a frame shift mutation into the coding region of MBP mRNA (FIG. 1, transcript B), deletion of 425 nt (including the polyA tail) from the 3' end (FIG. 1, transcript C) or deletion of the coding region (FIG. 1, transcript Previous experiments have demonstrated that the presence or absence of 5' cap also does not affect the distribution pattern of microinjected mRNA (Ainger et al., 1993). Thus, the 5' cap, the nascent MBP polypeptide, the coding region, the polyA tail, and the 3' 425 gases of the MBP mRNA are not required for granule assembly, transport or localization.

When the 3' mUTR region from position 1131–1473 was deleted from MBP mRNA (FIG. 1, transcript D), granules were observed in the perikaryon and processes, but were absent from the myelin compartment (FIGS. 15C and 15D), indicating that this region contains signals required for localization, but not for granule assembly or transport. Deletion of the region from position 953–1131, also in the 3' UTR (FIG. 1, transcript E) showed the same distribution as the transcript D, FIG. 1, indicating that this region also is not required for granule assembly or transport. It is not known if this region is required for localization, since, in the absence of the region from position 1131–1473, localization did not occur.

When the 3' UTR region from position 667–953 of MBP mRNA was deleted (FIG. 1, transcript F), granules were observed in the perikaryon, but not in the processes or myelin compartment (FIGS. 15E and 15F), indicating that this region contains signals required for granule assembly, but not for transport. The same distribution was observed when control RNAs encoding globin, a cytosolic protein (FIG. 1, transcript J), and actin, a cytoskeleton protein (FIG. 1, transcript L) were injected.

When the entire 3' UTR region of MBP mRNA (containing the putative transport and localization signals delineated above) was attached to globin mRNA (FIG. 1, transcript H), granules were observed in the perikaryon, processes and myelin compartment, indicating that this region is sufficient to confer transport and localization to a heterologous mRNA. When the region from position 667–953 (containing the putative transport signal but not the localization signal) was attached to globin mRNA (FIG. 1, transcript I), granules were observed in the perikaryon and processes, but not in the myelin compartment, indicating that this region is sufficient to confer transport but not localization to a heterologous mRNA. These results delineate two distinct regions in the 3' UTR of MBP mRNA: one region (nt 667–953) that contains signals for transport, and a second region (nt 1131–1473) that contains signals required for localization.

When RNAs smaller than approximately 500 bases were injected into oligodendrocytes, such RNAs moved non-specifically throughout the perikaryon, processes and myelin compartment, presumably due to diffusion. Therefore, in order to assay specific transport and or localization signals, it was essential to inject RNAs greater than 500 bases, and to use appropriate size matched controls. Accordingly, to assay the transport and localization properties of the 3' UTR region from 667–953 in the absence of other MBP mRNA sequences, the RNA was extended with non-specific vector-derived RNA sequences (FIG. 1, transcript K). With this RNA, granules were observed in the perikaryon, processes and myelin compartment (FIG. 15A), indicating that in the absence of a coding region, the region from nt 667–953 is sufficient for both transport and localization. These results are in contrast to results with RNA containing the region from nt 667–953 attached to the coding region from either MBP mRNA (FIG. 1, transcript E) or globin mRNA (FIG. 1, transcript I) which was transported but not localized. The discrepancy is likely due to either the coding regions containing elements which inhibit localization in the absence of the specific localization region from MBP mRNA, or the vector sequences in FIG. 1, transcript K, containing elements that mediate localization.

EXAMPLE 3

Sequence Analysis of the MBP mRNA

Sequence comparison methods were used to identify conserved elements within the regions delineated by deletion analysis. Computer analysis of sequence information was performed with the Genetics Computer Group program, 1991, Program Manual for the GCG Package, version 7, Madison, Wis., U.S.A. Rat 14K MPB (Roach et al., 1983) and mouse 14K MBP (Takahashi et al., 1985, *Cell* 42: 139–148) were used for sequence comparisons. The other sequences listed in FIG. 3 have the following GenEMBL accession numbers: rat c-jun, X17163; N-type calcium channel alpha-1, M94172; human clathrin light chain b, M20469 and J04174; human chromogranin A, J03483; nitric oxide synthase, M95674; bovine GABA(A) receptor, X05717; HIV-2 tat, vpr, J04542; human glycogen phosphorylase, J03544, human MBP, M13577; ras inhibitor, M37191; mouse heparin binding protein 44, D00622; RNA binding protein (FLI-2), M99167; mouse MAP 2A, M21041; mouse protamine 2, X14004; rat neurogranin (RC3), L09119; GFAP, K01347; mouse cyritestin, X64227; rat ARC, U19866; rat MOBP81-A, X87900; human N-type calcium channel alpha-1, M94172; bovine nitric oxide, M95674; puffferfish NCAML1, Z71926; rat atrophin-1 related protein, U44091; rat furosemide sensitive K-CL cotransporter, U55815; mouse protein kinase C alpha, M25811; human LIM kinase, D26309; human insulin like growth factor I receptor, X04434; mouse RNA binding protein (FLI-2), M99167; hepatitis C virus NS-5 region, Z35506.

The region in MBP mRNA containing the transport element was compared with other mRNAs that have been shown to be transported in other systems. First, the entire rat MBP sequence was compared to a set of transported mRNAs, including myelin associated/oligodendrocytic basic protein (MOBP 81A), which is localized to oligodendrocyte processes (Holz et al. 1996 *J. Neurosci.* 16:467–477), glial fibrillary acidic protein (GFAP), which is localized in astrocyte processes (Sarthy et al., 1989, *Mol. Cell. Biol.* 9(10):4556–4559), microtubule associated protein (MAP) 2A and activity regulated cytoskeleton-associated protein (ARC) which are localized to dendrites of hippocampal neurons (Garner et al., 1988, *Nature* 336:674–677; Link et al., 1995 *Proc. Natl. Acad. Sci. USA* 92:5734–5738; Lyford et al., 1995 *Neuron* 14(2):433–445), neurogranin (RC3), which is localized in neurons (Landry et al., 1994, *Brain Res. Mol. Brain Res.* 27(1):1–11), N-type calcium channel (Ca-N), GABA receptor alpha subunit (GABAR(A)) and nitric oxide synthase (NOS) which are localized to dendritic growth cones (Crino et al. 1996 *Neuron* 17:1173–1187), and protamine 2 which is localized in spermatocytes (Braun et al., 1989, *Genes and Devel.* 3:793–802).

As depicted in FIG. 3, a 21 nt sequence from 794 to 814 in the 3' UTR of rat 14K MBP which is conserved in mouse and human MBP mRNA, is homologous to sequences in the 3' UTR of MOBP81A, GABA R(A) and protamine 2, the coding regions of GFAP, Ca-N, MAP2A and ARC, and the 5' UTR of NOS and RC3. The regions of homology have 13 or more identical bases within the 21 base segment. In the case of MOBP 81A and MAP 2A, the homologous sequences are present in localized mRNA isoforms, but absent from nonlocalized isoforms (Holz et al. 1996; Kindler et al., 1996, *Brain Res. MOl. Brain Res.* 36(1):63–69) indicating that the region containing this sequence is necessary for transport of these mRNAs as it is for MBP mRNA. In the case of protamine 2, the homologous sequence is present in a region of the mRNA that is required for localization in spermatocytes (Braun et al., 1989). Furthermore, protamine 2 mRNA (containing the homology region) is transported when microinjected into oligodendrocytes indicating that the 3' UTR of protamine 2 mRNA contains sequences that can mediate transport in oligodendrocytes.

The putative transport element of 21 nucleotides in length was designated the RNA transport sequence (RTS). Close inspection of the 21 base RTS consensus sequence shown in FIG. 3 reveals that it contains two partially overlapping homologous decanucleotide sequences: GCCAAGGAGC (SEQ ID NO:31) and GCCAGAGAGC (SEQ ID NO:32) differing only by inversion of an AG dinucleotide in the center of the sequence. Most of the transported mRNAs in FIG. 3 contain perfect or almost perfect matches to one or the other of these decanucleotide sequences.

If the RTS is a general transport signal, it should be present in other transported RNAs. Although it is not known whether the RNAs (other than MBP) listed in FIG. 3 containing the RTS homology region are transported, the presence of sequences homologous to the RTS suggests that they may be. It is likely that the RTS comprises a general RNA transport signal that is utilized in a variety of different systems. Although all the previously described transport elements are in 3' UTRs, some of the RTS homologies were unexpectedly found within coding regions. In all the mRNAs containing an RTS-like sequence within the coding region, the translational reading frame is the same with respect to the RTS as indicated in FIG. 3. There are some differences in the peptide sequences due to bases which do not match the consensus.

The RTS containing regions of MBP are flanked by U rich repeats which have a consensus of CUUUSUUU (SEQ ID NO: 1) where S is either C or G. There are three repeats in rat, mouse and human MBP mRNA. Some of the RTS-containing mRNAs in FIG. 3 also have U rich sequences flanking the RTS. The RTS of MBP mRNAs is adjacent to a motif involved in the localization of β-actin mRNA to the lamellipodia of fibroblasts (Kislauskis et al., 1994 *J. Cell Biol.* 127: 441–451). This motif, GGACT, (SEQ ID NO:2) occurs 8 to 12 bases downstream of the RTS in rat, mouse and human MBP mRNA.

In summary RNA transport sequences (RTSs) from the 3' UTRs of rat, mouse and human MBP have been identified. Both rat and mouse have the following 21 nt sequence:

5' GCCAAGGAGCCAGAGAGCAUG 3' (SEQ ID NO:3)

In human, there are two MBP RTSs. The first RTS (RTS1) has the following sequence:

5' GCUGCAGAGACAGAGAGGACG 3' (SEQ ID NO:4)

The second RTS in human (RTS2), has the following sequence:

5' GCCAUGGAGGCACACAGCUG 3' (SEQ ID NO:5)

EXAMPLE 4

Predicted Secondary Structure of the MBP 3' UTR

Figure 4A:
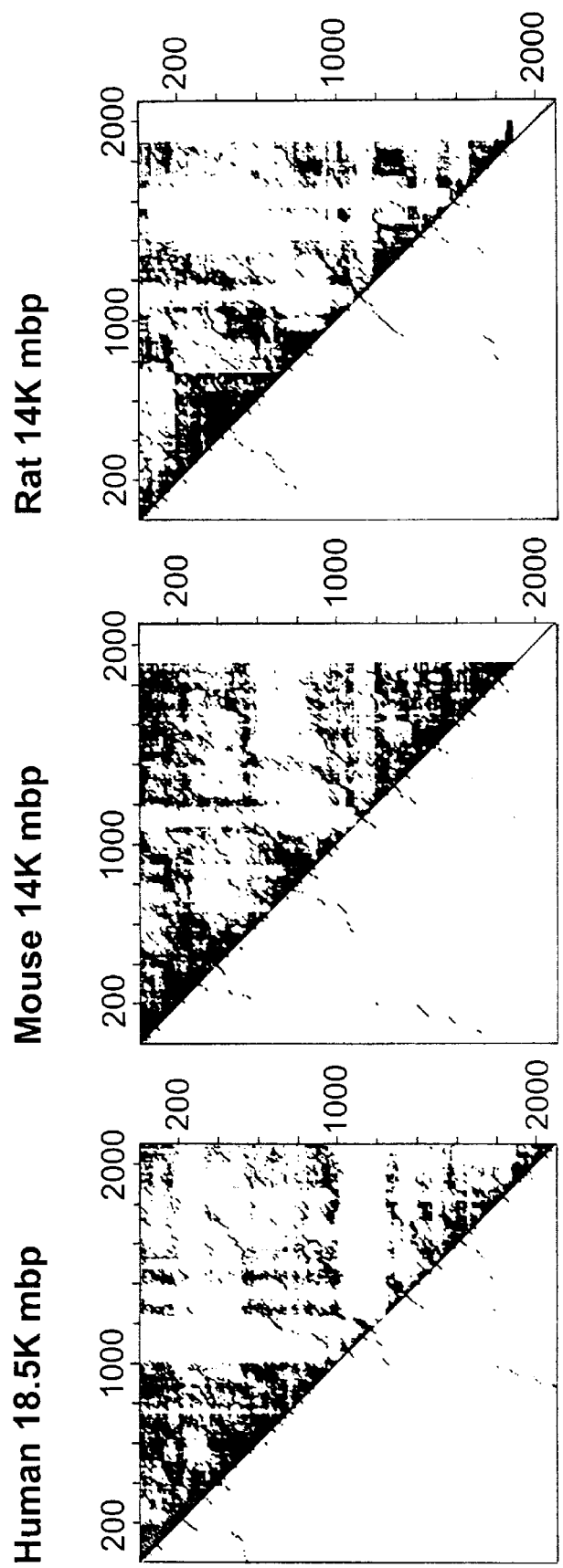
FIG. 4A depicts energy dotplots of rat 14K, mouse 14K, and human 18.5K MBP RNAs showing suboptimal structures within 10 kcal/mole of the optimal structures are plotted above the diagonal. Sparsely populated vertical and horizontal regions indicate possible stable structures. Optimal structures are plotted below the diagonal.
Figure 4B:
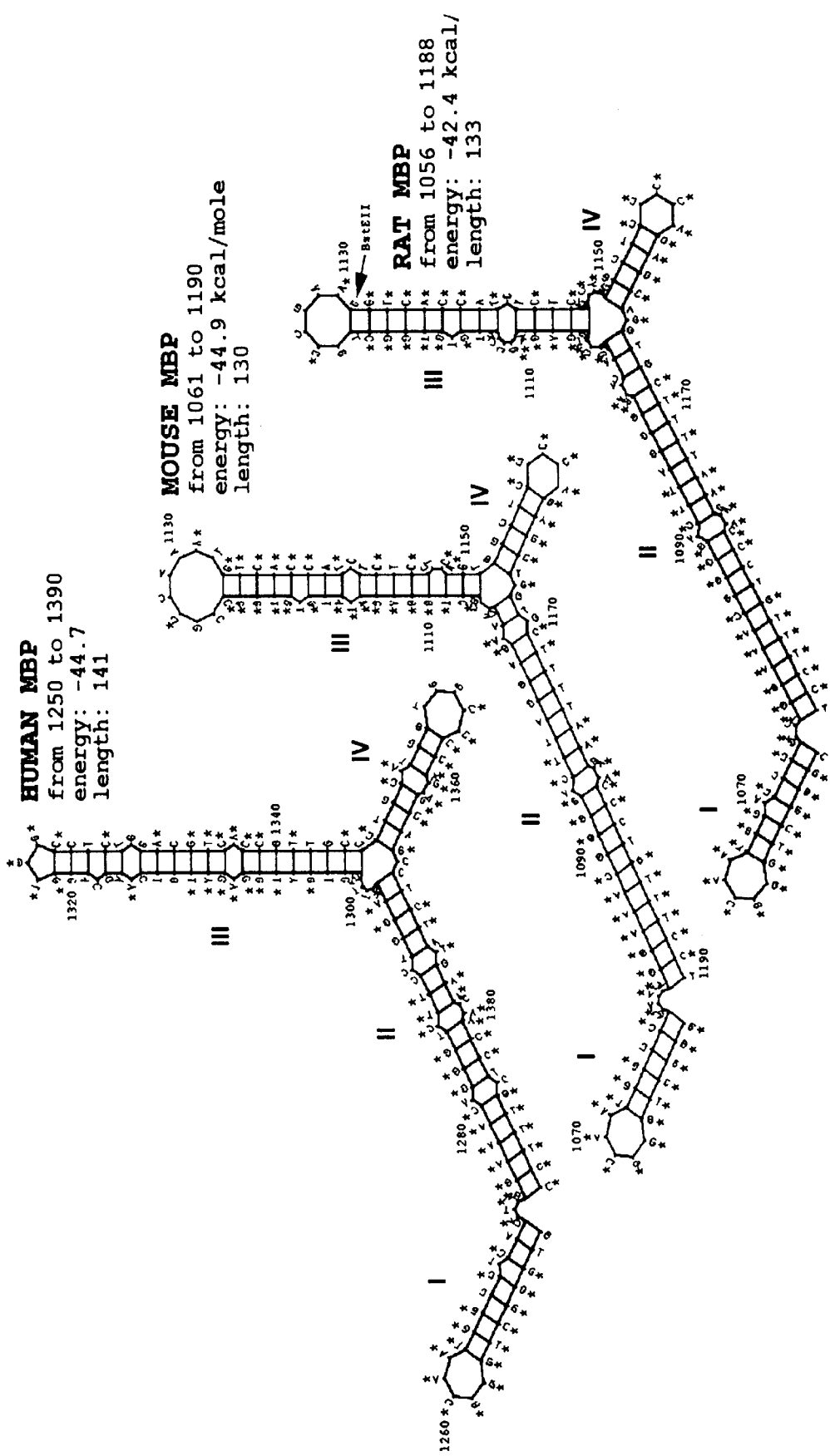
FIG. 4B shows rat 14K MBP mRNA secondary structure from base 1056 to 1188, mouse 14K mRNA structure from 1061 to 1190, and human MBP 18.5K mRNA structure from base 1250 to 1390. Asterisks denote bases conserved in rat, mouse and human MBP mRNAs. The BstEII site used to create the RNA in FIG. 1D is indicated on the rat structure.

In order to identify potential RNA secondary structures that might be present in the MBP 3' UTRs, the rat, mouse and human MBP mRNA sequences were analyzed with the MFOLD program of Zuker (Jacobson et al., 1993, *J. Mol. Biol.* 233(2): 261–269). The results of the secondary structure predictions are shown in FIG. 4. In FIG. 4A, the suboptimal energy dotplots of rat 14K MBP mRNA, mouse 14K MBP mRNA, and human 18.5K MBP mRNA display predicted structures within 10 kcal/mole of the predicted optimal structures. Low energy, and therefore stable, structures are indicated by sparsely populated horizontal and vertical areas in the suboptimal energy dotplot. The RTS-containing regions of rat (667–953), human or mouse MBPs have no well determined structures. A single well determined structure is present within the region required for RNA localization (in rat MBP mRNA from 1056 to 1188, and in mouse MBP mRNA from 1061 to 1190). Human MBP has two well determined structures within the 3' UTR. One structure, from 1004 to 1248 is just downstream of the RTS region (927 to 967). It is followed by a smaller structure from 1250 to 1390. The regions for rat and mouse MBP mRNA containing the predicted secondary structures share about 70% sequence identity with the region containing the smaller of the human secondary structures. Predicted structures for the corresponding regions for rat, mouse and human MBP mRNAs are shown in FIG. 4B. The overall structures and the distance from the RTS is conserved in each despite significant sequence diversity. In order to estimate the significance of the predicted secondary structures in the MBP mRNAs, several other mRNAs were analyzed with the MFOLD program. The number, shape and position of predicted secondary structures of the mRNAs of 2',3'-cyclic nucleotide 3'-phosphodiesterase (CNPase) (Bernier et al., 1987 *J. Neurosci.* 7:2703–2710), Vg1 (Weeks et al. 1987, *Cell* 51:861–867), and GFAP were different than the MBP mRNAs. These mRNAS were selected because one is expressed by oligodendrocytes (CNPase) and the other two are transported mRNAs. Disruption of the potential structure in MBP mRNA by deletion interferes with localization of microinjected RNA. The enzyme site (BsteII) used to create the template construct for transcript D in FIG. 1 is indicated on the rat MBP RNA structure. Truncation of the RNA at the BstEII site shown in rat MBP mRNA, interferes with localization (as shown by the RNA in FIG. 1, transcript D), indicating that disruption of the potential structure in MBP mRNA by deletion interferes with localization. These results indicate that predicted secondary structures shown in FIG. 4B likely comprise a localization element necessary for localization of MBP mRNA to the myelin membranes.

EXAMPLE 5

Determination of RTS Transport Efficiency

In order to determine whether the RTS contains enough of the 3'UTR (apart from those sequences identified in Example 2) to confer transport of an mRNA transcript, chimeric RNA transcription templates were constructed using the RTS and coding sequence for Proteolipid protein (PLP). First, an oligonucleotide containing the RTS sequence with SpeI and KpnI linkers (CTAGTGCCAAGGAGCCAGAGAGCATGGGTAC) (SEQ ID NO: 33) was cloned into SpeI/KpnI digested pBluescriptII (SK) to generate the plasmid pRTS. To construct the PLP-RTS chimeric RNA, PLP cDNA (F. Smith, Shriver Center) was digested with SpeI and KpnI, removing 560 nucleotides from the PLP 3' UTR and ligated to Spe/KpnI digested PRTS. The resulting plasmid was linearized with KpnI, blunt ends were created with the Klenow fragment and transcribed with T3 RNA polymerase.

Figure 12:
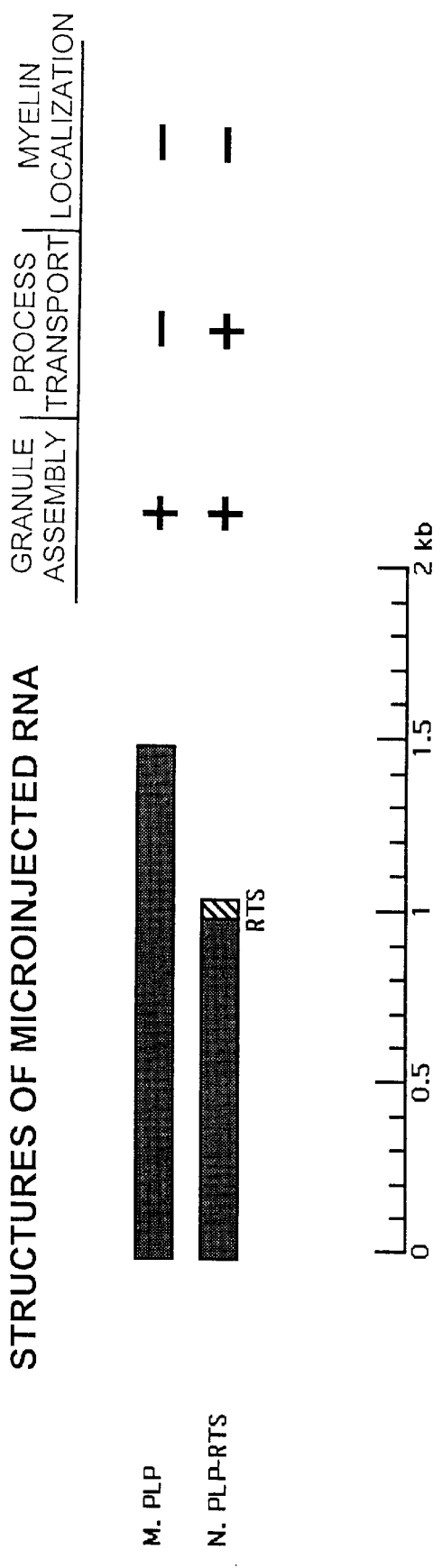
FIG. 12 depicts structures of two RNA transcripts made from templates containing proteolipid protein (PLP) mRNA (Transcript M) and PLP mRNA and RTS (Transcript N). Plus (+) indicates mRNA distribution was observed in a majority of the injected cells for each of transcript M and N.

Both PLP mRNA and PLP-RTS mRNA were microinjected into oligodendrocytes as described in Example 2. When PLP RNA (FIG. 12, transcript M) was injected into oligodendrocytes, the distribution pattern in FIG. 13C was observed. The RNA was assembled into granules that were confined to the perikaryon and not transported along the processes or localized to the mylein compartment, indicating that PLP does not contain transport or localization signals. In contrast to other nontransported RNAs such as globin mRNA, which were uniformly distributed within the perikaryon, PLP RNA was concentrated in the perinuclear region of the cell and the distribution appeared nonuniform and somewhat reticular.

Since PLP mRNA is known to be translated on membrane bound polysomes, the cells were also labeled with antibody to BIP, a lumenal protein specific for the ER (Haas et al., 1983, *Nature*, 306:387–389) following standard procedures. Such labeling allowed visualization of the distribution of the ER within the cell. As shown in FIG. 13D, the ER appears as reticular network distributed throughout the perikaryon and proximal processes, but concentrated in the perinuclear region. Comparison of the distribution of PLP RNA (FIG. 13C) and BIP (FIG. 13D) indicates that PLP RNA granules are concentrated in the perinuclear regions where BIP labeling is most intense. Since cotranslational association of mRNA with the ER is mediated by the nascent polypeptide chain, this result indicates that microinjected PLP mRNA is translated in the oligodendrocyte perikaryon and associates cotranslationally with the ER through sequences in the nascent PLP polypeptide. Furthermore, since PLP RNA appears as granules, translation does not interfere with granule assembly, nor does granule assembly prevent translation or association with ER.

PLP-RTS RNA (FIG. 12, transcript N) was assembled into granules that were transported to the processes but not localized to the myelin compartment (FIGS. 13A and B). These results indicate that the RTS is necessary and sufficient for transport along the processes but not for localization to the myelin compartment. Without the RTS, PLP RNA granules appeared in a reticular distribution in the perinuclear region. Insertion of the RTS into PLP-RTS RNA resulted in a more dispersed distribution of granules throughout the perikaryon and processes. If the perinuclear distribution of PLP RNA reflects cotranslational association of PLP RNA with ER, the more dispersed distribution of PLP-RTS presumably reflects RTS mediated transport of the injected RNA prior to cotranslational association with ER.

Figure 14:
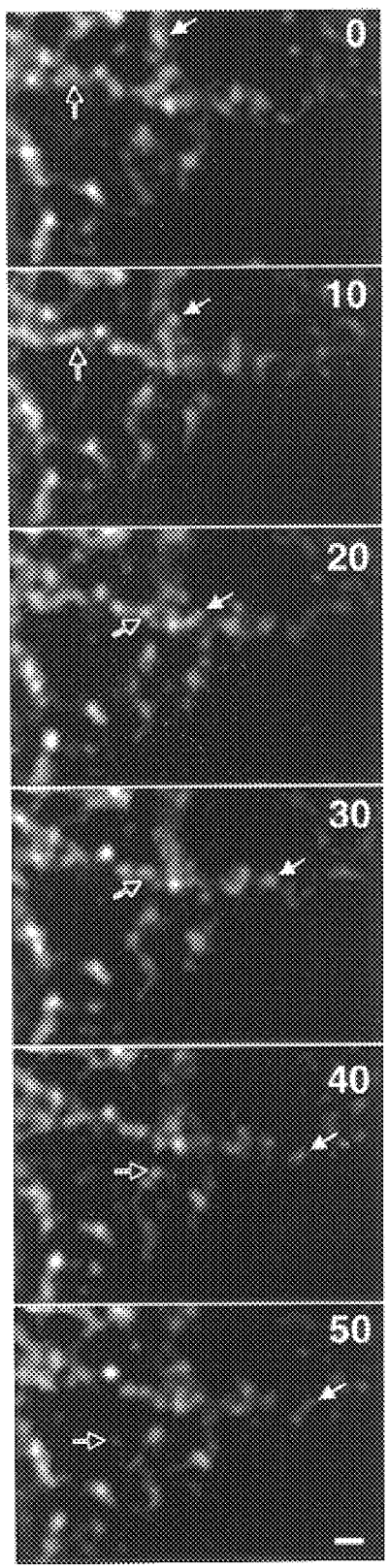
FIG. 14 is a time lapse confocal imaging (ten second intervals) of RNA movement in oligodendrocyte microinjected with fluorescent PLP-RTS RNA. The region shown contains several oligodendrocyte processes. The cell body is out of the frame to the left. Two granules (indicated by open and closed arrows) exhibited sustained vectorial motion in an anterograde direction during the time course shown. The scale bar represents 1μ.

Thus, insertion of the RTS into either GFP or PLP mRNA results in redistribution of the RNA from the perikaryon to the processes. To rule out the possibility that GFP and PLP RNA contain perikaryon retention signals which are disrupted by insertion of the RTS, allowing the RNA to move to the processes by passive diffusion, fluorescently labeled PLP-RTS RNA was mircoinjected and visualized in living cells by time lapse confocal microscopy. A series of frames showing portions of several processes from an injected oligodendrocyte is shown in FIG. 14. The majority of labeled granules in the processes are immobile. At least two labeled granules, however, (indicated by arrows) exhibit sustained anterograde vectorial motion (mean displacement 0.1–0.2 $\mu$/sec) during the time course shown. These results demonstrate directed RNA transport of at least some RTS-RNA containing granules.

EXAMPLE 6

Determination of Translational Efficiency of MBP RTS Using an In Vivo Translation Assay To determine whether the MBP RTS can also function as a cis-acting translational regulatory element, an in vivo translation assay using green fluorescent protein (GFP) from *Aequorea victoria* as a reporter for translation was developed. GFP mRNA and chimeric GFP mRNA, containing the MBP RTS in the 3' UTR, were prepared by in vitro transcription and microinjected into neuroblastoma B104 cells and CHO cells.

Neuroblastoma B104 cells and CHO cells were grown in 6% newborn calf serum in Dulbecco Modified Eagles medium (DME) following the procedure of Ainger et al., 1993. Shiverer oligodendrocytes were isolated after 12–14 days of growth in culture as described previously (Ainger et al., 1993).

Restriction enzymes and RNA polymerase were obtained from New England BioLabs (Beverly, Mass.), Promega (Madison, Wis.), Stratagene (La Jolla, Calif.), and Epicentre Technologies (Madison, Wis.). RNA and protein molecular markers were obtained from Molecular Probes, Inc. (Eugene, Oreg.).

Full length cDNA for a S65T mutant GFP cloned in pRSETB, was obtained from Dr. R. Y. Tsien (University of California, San Diego, Calif.). pGEM1A, containing the SP6 promoter and poly a track, was obtained from Dr. G. Carmichael (University of Connecticut Health Center, Farmington, Conn.). The entire S65T mutant GFP cDNA was subcloned into the BamH1 site of pGEM1A to create PGFP'A. An oligonucleotide comprising a sequence of deoxyribonucleotides corresponding to the RTS (GCCAAGGAGCCAGAGAGCATG)(SEQ ID NO:2) was inserted into AvaI/SacI cut pGFP'A and Hind III/XbaI cut pGFP'A to create pGFP'3RTS and pGFP'5RTS, respectively. To create pGFP'53RTS, the RTS was inserted into both AvaI/SacI and HindIII/XbaI cut pGFP'A.

GFP mRNA and chimeric GFP mRNA, containing the RTS in either the 3'UTR, the 5'UTR, or both 5'UTR and 3'UTR, were prepared by in vitro transcription using Ampi Scribe SPG Transcription Kits (Epicentre Technologies) following the instructions of the manufacturer. PGFP'A, pGFP'3RTS, pGFP'5RTS, and pGFP'53RTS, linearized with SapI, were used as template DNA and m7G(5')ppp(5')G was added to the transcription mixture to produce capped mRNA's.

In Vivo Translation Assay

Figure 5:
FIG. 5 is a scheme which depicts the in vivo translation assay used to demonstrates that the RTS from MBP functions as a cis-acting translational regulatory element.
Figure 5:
Figure 5:

Capped GFP'A mRNA and GFP'3RTS mRNAs were microinjected into neuroblastoma B104 cells, CHO cells, and shiverer oligodendrocytes, respectively as described previously (Ainger et al., 1993). Texas Red-conjugated dextran was coinjected to normalize for the amount of injected mRNA. The amount of injected RNA is derived from the intensity of Texas Red-conjugated dextran in the cell. Injected cells were incubated at 37° C. for 20–24 hours. The expressed GFP/Texas Red intensities were determined by dual channel confocal microscopy, using an Axiophot microscope (Zeiss, Oberkochen, Germany) with a MRC 600 confocal laser scanning system (Biorad, Hercules, Calif.). Images were collected using a Nikon 60X 14 N.A. objective. The in vivo translation assay scheme is depicted in FIG. 5.

Figure 6A:
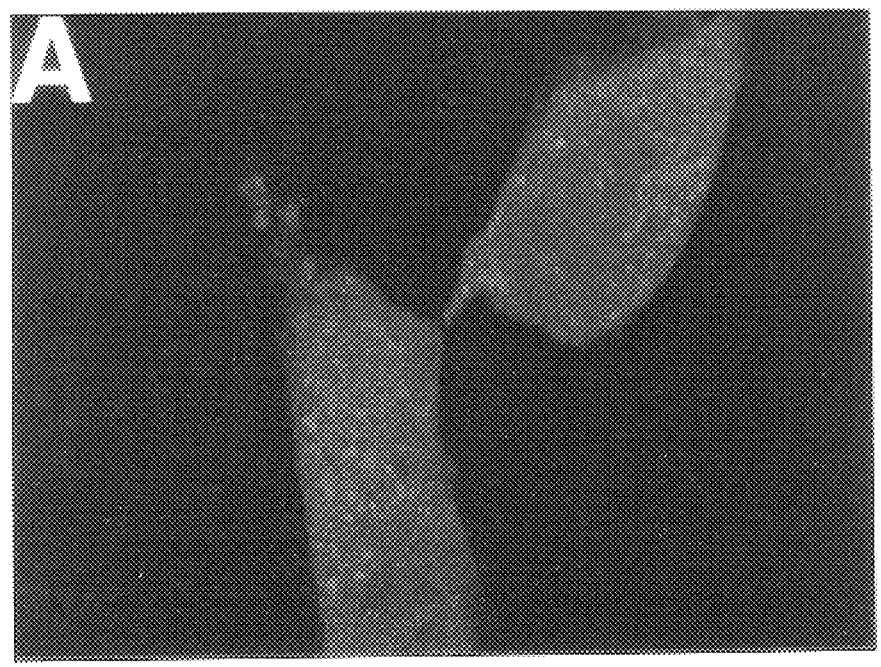
FIGS. 6A and 6B are dual channel confocal images of neuroblastoma B104 cells microinjected with in vitro transcribed GFP mRNA. The red channel shows Texas Red-conjugated dextran as a measure of the volume injected. The green channel shows GFP expression.
Figure 6B:
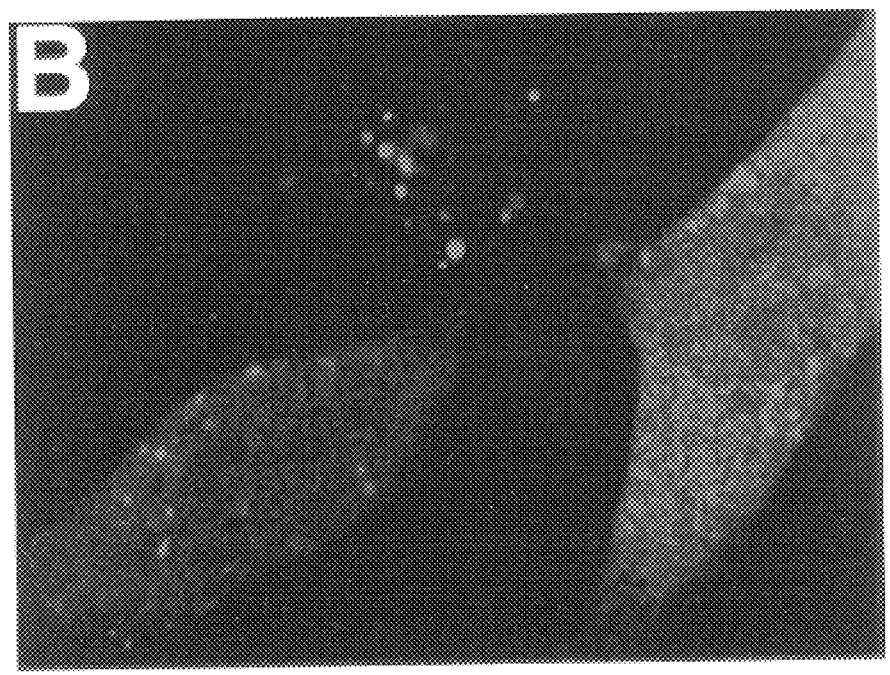
Figure 6C:
FIGS. 6C and 6D show dual channel confocal images of neuroblastoma B104 cells microinjected with in vitro transcribed GFP/RTS(3') fusion mRNA. The red and green channels are as described for FIGS. 6A and 6B.
Figure 6D:
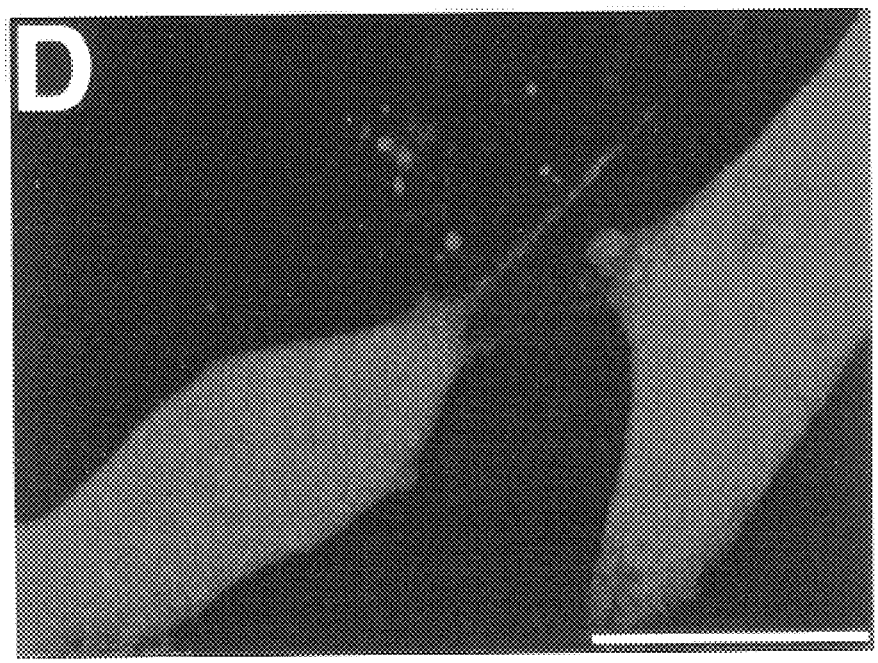

Results of the microinjection experiments are depicted in FIGS. 6A through 6D. FIGS. 6A and 6B are dual channel confocal images of neuroblastoma B104 cells microinjected with in vitro transcribed GFP mRNA. FIGS. 6C and 6D show dual confocal images of neuroblastoma B104 cells microinjected with in vitro transcribed GFP/RTS(3') fusion mRNA. The red channel shows Texas Red-conjugated dextran as a measure of the volume injected. The green channel shows GFP expression. From the intensity of the red channel in FIGS. 6A and 6C, it can be concluded that the cells were injected with approximately equal amounts of Texas Red-conjugated dextran, indicating that approximately equal volumes of GFP mRNA and GFP/RTS(3') mRNA were microinjected. The intensity of the green channel in FIG. 6D however, appears much brighter than the intensity of the of the green channel in FIG. 6B. These results indicate that the RTS effects an increase in translation in the GFP/'RTS(3') mRNA transcript.

Figure 7:
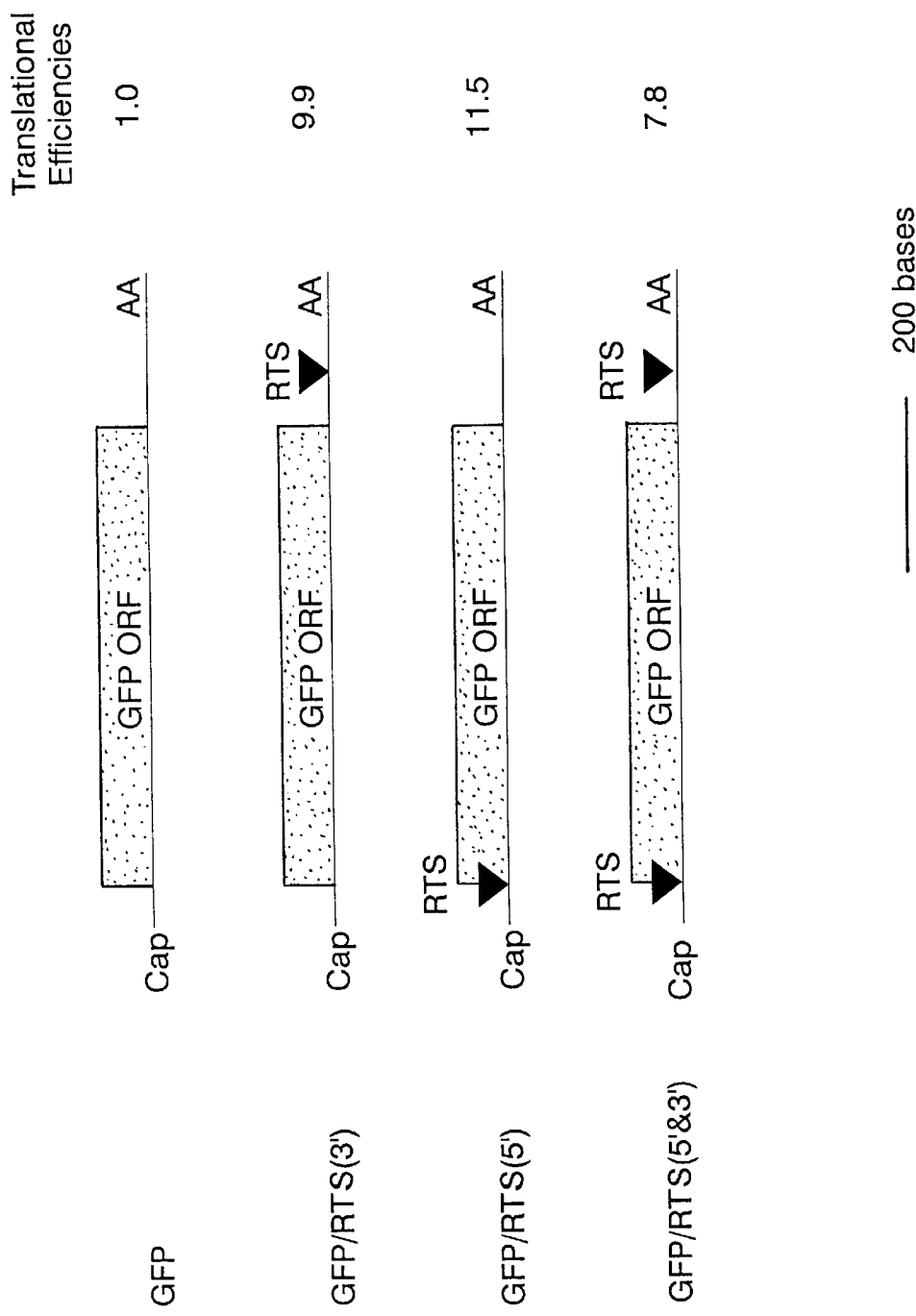
FIG. 7 is a schematic diagram representing in vitro transcribed GFP MRNA and GFP/RTS fusion mRNAs. Translational efficiencies are indicated to the right.
Figure 8A:
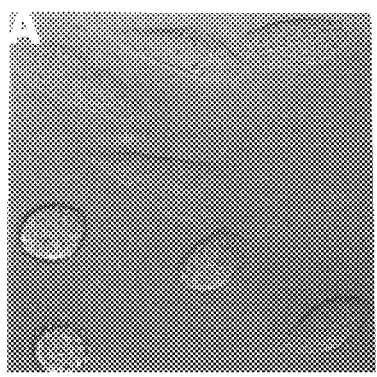
FIG. 8A is a scanning transmitted light image of CHO cells microinjected with in vitro transcribed GFP mRNA.
Figure 8B:
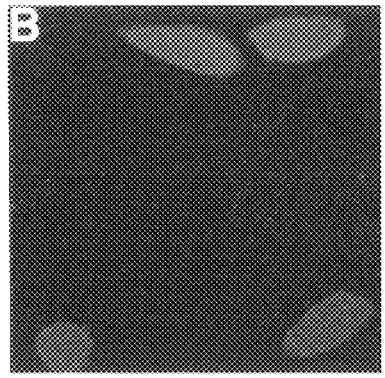
FIG. 8B is the red channel of a confocal image of CHO cells shown in 8A microinjected with in vitro transcribed GFP mRNA and Texas Red-conjugated dextran.
Figure 8C:
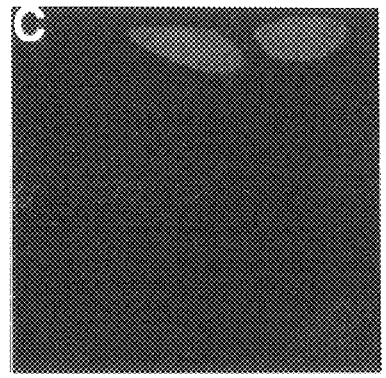
FIG. 8C is the green channel of the confocal image shown in FIGS. 8A and 8B of CHO cells microinjected with in vitro transcribed GFP mRNA and Texas Red-conjugated dextran.
Figure 8D:
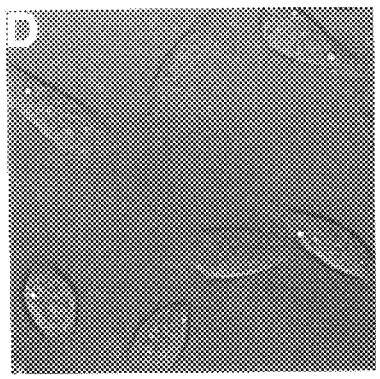
FIGS. 8D, 8F, and 8E are the same as FIGS. 8A–8C except with GFP/RTS(3') RNA and Texas Red-conjugated dextran.
Figure 8E:
Figure 8F:
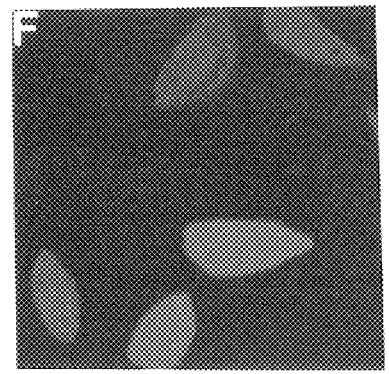

Translational efficiencies were determined by measuring the GFP/Texas Red ratios at subsaturating levels. Results of the assay are depicted in FIG. 7. As FIG. 7 indicates, the position and number of RTSs do not effect translational efficiency.

Figure 9:
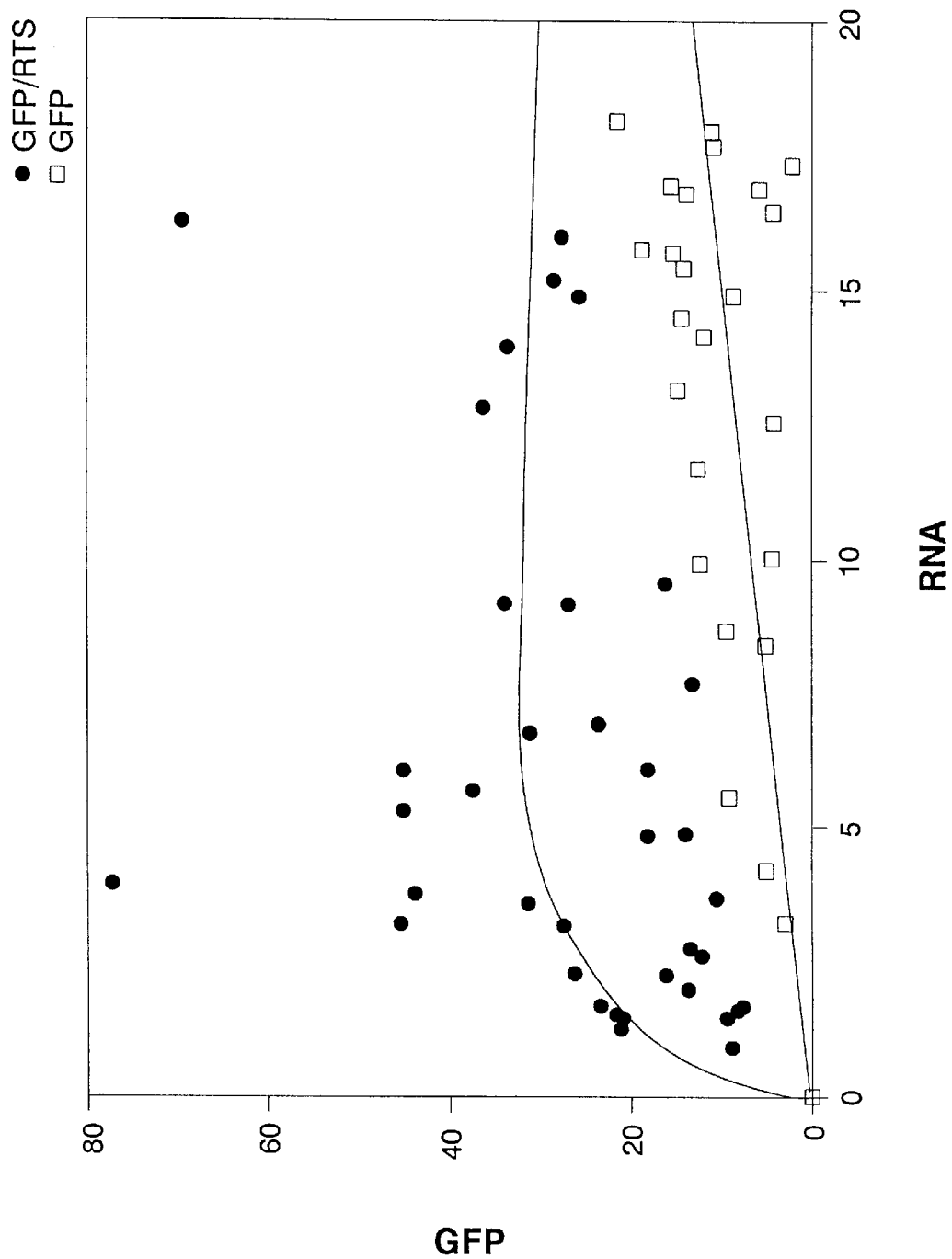
FIG. 9 is a graph illustrating dose response of GFP expression in neuroblastoma B104 cells microinjected with in vitro transcribed GFP mRNA and GFP/RTS(3') mRNA. The GFP values are arbitrary intensity units. The amount of injected RNA is derived from the intensity of Texas Red-conjugated dextran in the cell.

As depicted in FIG. 9, the GFP/RTS(3') mRNA is translated more efficiently than the GFP mRNA. At high amounts of mRNA, the translational machinery appears to be saturated.

Microinjection results using CHO cells are shown in FIGS. 8A through 8F. Similar to the results achieved in neuroblastoma cells (FIGS. 6A through 6D), cells microinjected with GFP/RTS(3') mRNA and visualized through the green channel (FIG. 8F) appear very bright when compared to cells microinjected with GFP mRNA (FIG. 8C) even though equal volumes of Texas Red-dextran and either GFP mRNA or GFP/RTS(3')mRNA were injected. There appears to be some variation in intensities and therefore translational efficiencies among CHO cells injected with GFP/RTS(3') mRNA.

In summary, the RTS causes an increase in translational efficiency of a heterologous mRNA transcript when present in the heterologous transcript. The RTS acts as a cis-acting translational enhancer sequence in both neuroblastoma B104 and CHO cells. Similar results were obtained with oligodendrocytes. Translational enhancement by the RTS is independent of its position in the mRNA.

EXAMPLE 7

Figure 10A:
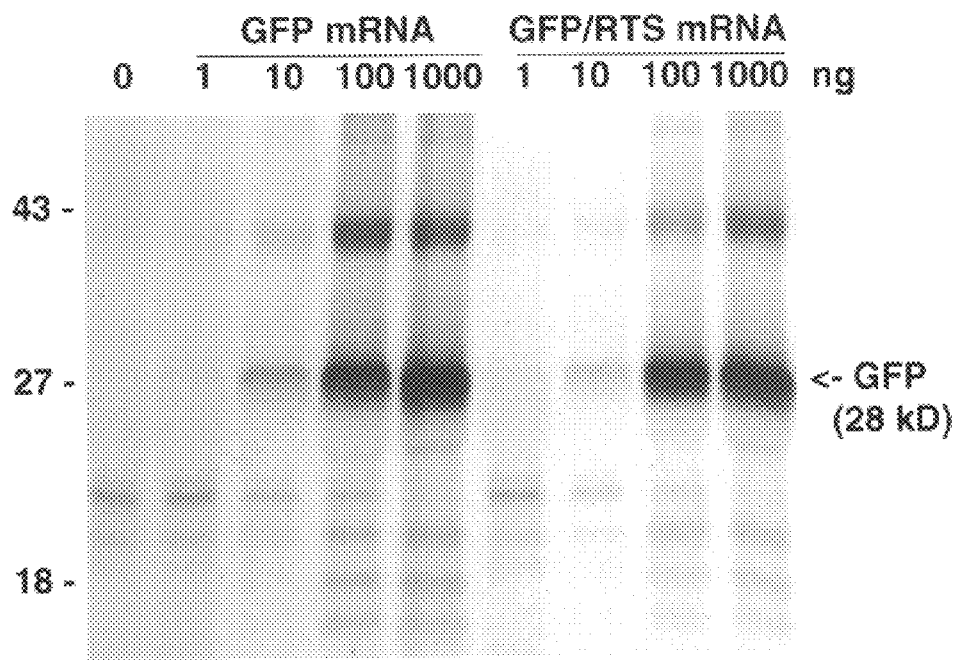
FIG. 10A is a photograph of a gel through which were electrophoresed various amounts of in vitro transcribed GFP mRNAs and GFP/RTS(3') mRNAs translated in a rabbit reticulocyte lysate.
Figure 10B:
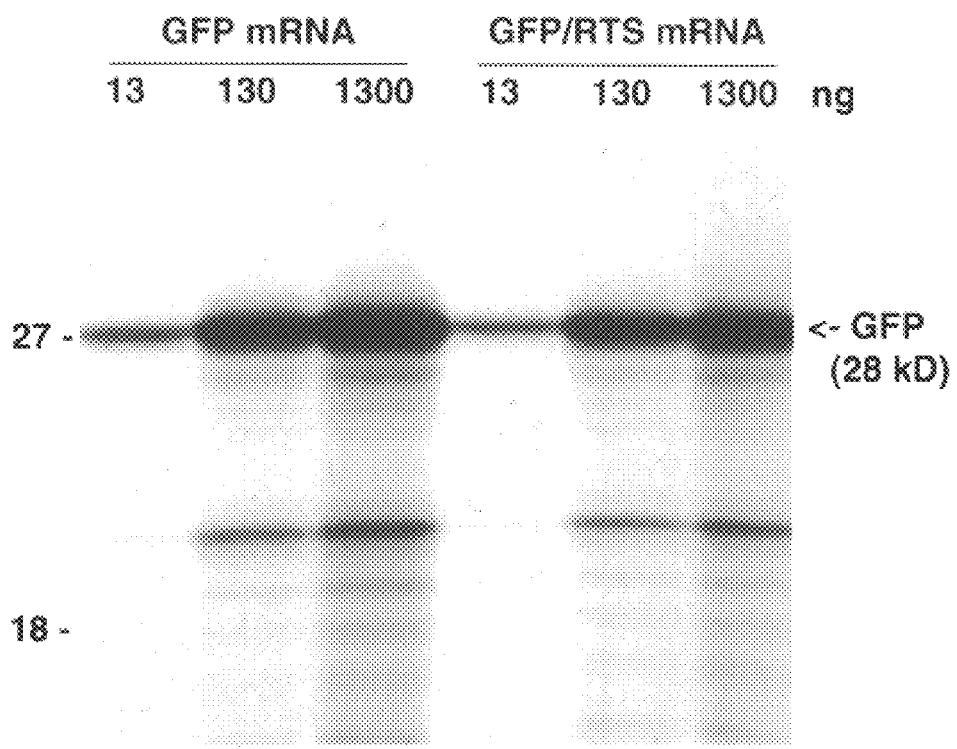
FIG. 10B is a photograph of a gel through which were electrophoresed various amounts of in vitro transcribed GFP mRNAs and GFP/RTS(3') mRNAs translated in a wheat germ extract.

Determination of Translational Efficiency of MBP RTS Using an In Vitro Translation Assay Nuclease treated rabbit reticulocyte lysate and wheat germ extracts were purchased from Promega and the reactions were performed according to the manufacturer's instructions. Translation of GFP was monitored by [35S] methionine (Amersham) incorporation into GFP polypeptides after 12% SDS-PAGE. After electrophoresis, the gels were fixed and soaked in EN3HANCE (New England Nuclear) before drying. As shown in FIGS. 10A and 10B, the amount of GFP translated is approximately the same for GFP mRNA and GDP/RTS(3') mRNA in both systems. Thus, the RTS does not affect in vitro translational efficiencies in either rabbit reticulocyte lysate or wheat germ extract. These results, when coupled with the results obtained in Example 6, indicate that the RTS functions as a cis-acting translational enhancer in living cells but not in vitro when present in a heterologous mRNA transcript.

EXAMPLE 8

In Vivo Translational Assay Using Humanized GFP as a Reporter

Figure 11:
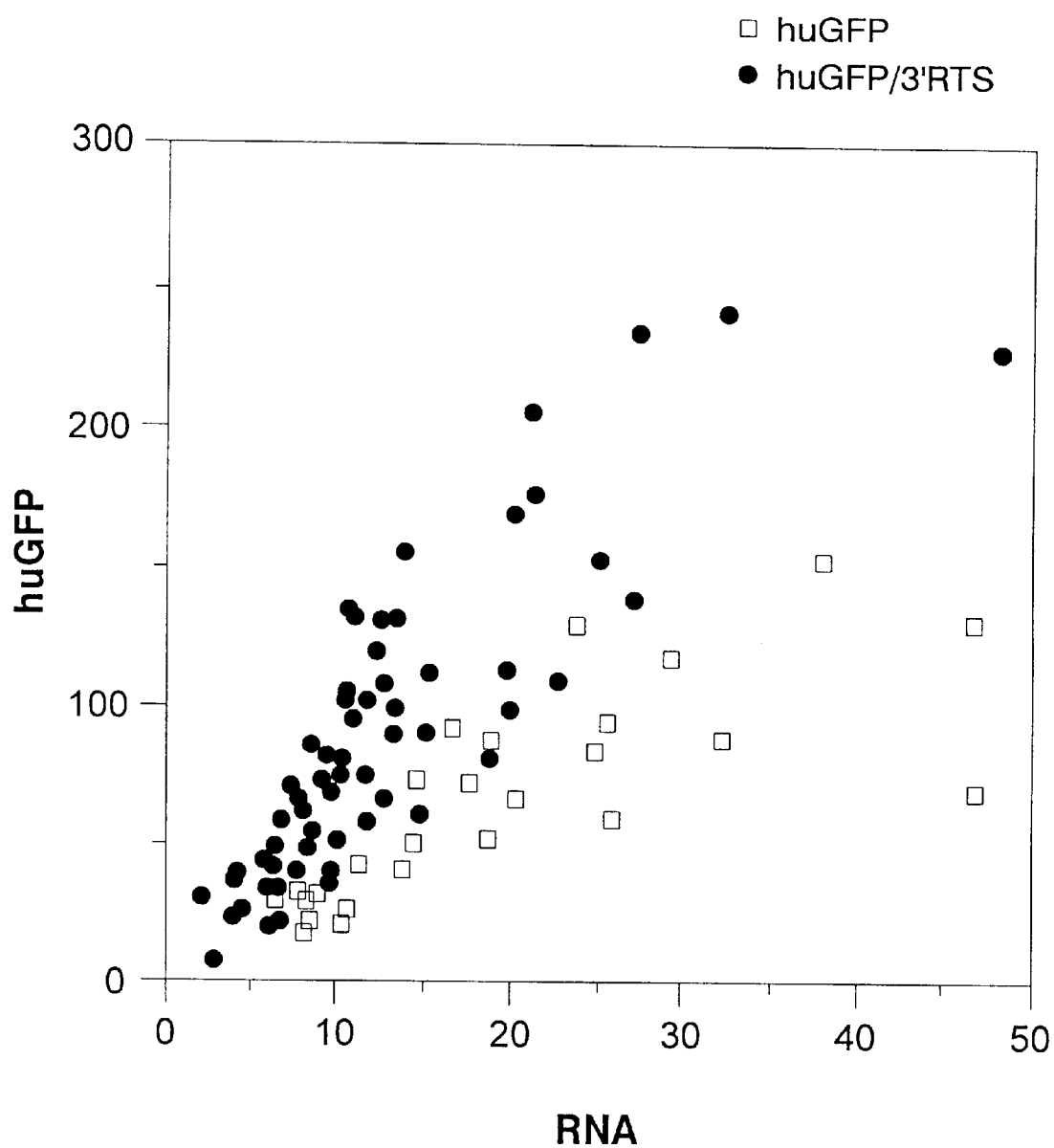
FIG. 11 is a graph illustrating dose response of humanized GFP (huGFP) expression in neuroblastoma B104 cells microinjected within vitro transcribed huGFP mRNA and huGFP/RTS(3') mRNA. The GFP values are arbitrary intensity units.

The coding region of a "humanized GFP" (huGFP) from plasmid pGREEN LANTERN-1, purchased from Life Technologies (Gaithersburg, Md.), was also used as a reporter for an in vivo translation assay. huGFP is a synthetic version of the jellyfish GFP, substituting preferentially used codons in the mammalian genome for the rarely used codons in the S65T mutant GFP. Therefore, huGFP contains a different mRNA sequence from S65T GFP. In vitro transcription and microinjection of capped huGFP mRNAs and huGFP/3' RTS mRNAs were as described for GFP'A and GFP13RTS mRNAS Of Example 6. As shown in FIG. 11, the cells which were injected with chimeric huGFP mRNA, containing the RTS in the 3'UTR expressed more GFP than the cells injected with the huGFP mRNA. This result indicates that the RTS acts as a general cis-acting translational enhancer for different mRNAs.

EXAMPLE 9

Transport of GFP mRNA in Oligodendrocytes Mediated by the RTS

The 21 nt RTS sequence from MBP mRNA (SEQ ID NO:3) was inserted into the 3' UTR of GFP mRNA as described in Example 6. These are the same transcripts made by the same methods as described in Example 6, i.e., pGFP'3RTS. Digoxigenin-labeled GFP RNA (+/–RTS) was synthesized by in vitro transcription and microinjected into oligodendrocytes as described in Examples 2 and 6. The cells were incubated for 60 minutes and then fixed and stained to visualize the distribution of the digoxigenin labeled RNA. In addition, the RNA was injected into oligodenrocytes that were treated with antisense oligonucleotide hnRNPA2 to suppress hnRNPA2 expression. The nucleotide sequence of hnRNPA2 is published (GenEMBL Accession Number M29065). hnRNPA2 binds specifically to the RTS sequence. Antisense oligonucleotide to hnRNPA2 was purchased from National Biosciences, Plymouth, N.H.

Laser scanning confocal microscopy was performed as described in Example 2. Cells in which the RNA was found in the distal processes were scored as transport positive (+). Cells in which the RNA was confined to the perikaryon were scored as transport negative (−). The experiment was repeated four times with 50–100 cells scored for each condition in each experiment. The results are expressed as % transport positive cells.

Figure 16:
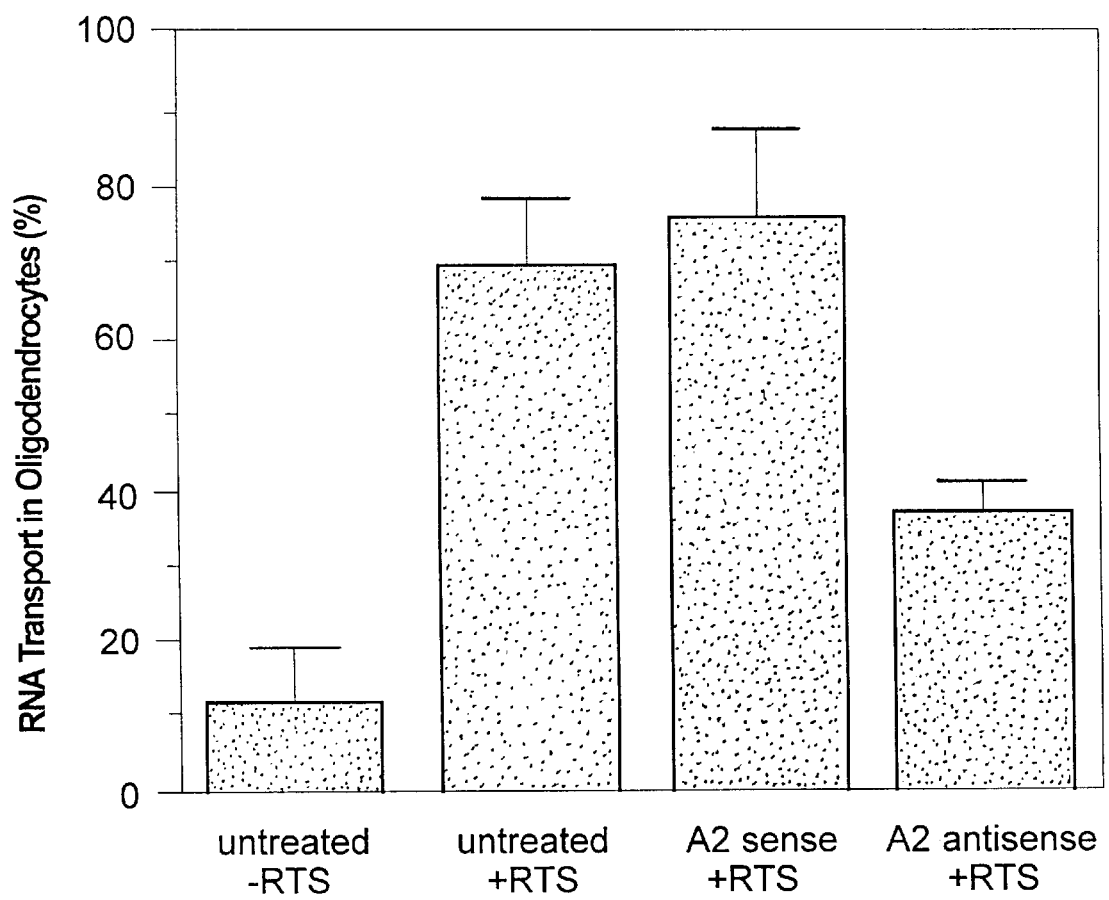
FIG. 16 graphically depicts transport of a GFP/RTS mRNA in microinjected oligodendrocytes which were either untreated or treated with sense and antisense oligonucleotides to hnRNPA2.

As depicted in FIG. 16, oligodendrocytes which were untreated, injected with the GFP/RTS mRNA, or treated with the sense oligonucleotide to hnRNPA2 and microinjected with GFP/RTS mRNA, exhibited transport of the RNA. Control oligodendrocytes injected with GFP RNA and oligodendrocytes which were treated with an antisense oligonucleotide to hnRNPA2 and microinjected with GFP/RTS mRNA did not exhibit transport of the GFP/RTS mRNA. These results confirm the results obtained in Example 5 for PLP-RTS RNA: the RTS directs transport of heterologous RNAs when present as part of the heterologous RNA transcript. These results also show that hnRNPA2 is required for RTS-mediated transport.

What is claimed is:

1. An isolated nucleic acid molecule consisting of a cis-acting mRNA transport sequence (RTS) of a myelin basic protein (MBP) cDNA or a portion thereof which enhances transport of mRNA within the cytoplasm.

2. The isolated nucleic acid molecule of claim 1 wherein said RTS consists of nucleotides 667 to 953 of an MBP cDNA or a portion thereof.

3. An isolated nucleic acid molecule consisting of a cis-acting mRNA localization enhancer (RLE) of a myelin basic protein (MBP) cDNA or a portion thereof which enhances localization of mRNA within the cytoplasm.

4. The isolated nucleic acid molecule of claim 3 wherein said RLE consists of nucleotides 1130 to 1473 of an MBP cDNA or a portion thereof.

5. An isolated nucleic acid molecule consisting of the sequence set forth in SEQ ID NO:3.

6. An isolated nucleic acid molecule consisting of a variant of SEQ ID NO:3; wherein the variation from SEQ ID NO:3 in said variant comprises at least one of an insertion, deletion, or substitution of one or more nucleotides, and wherein said isolated nucleic acid molecule enhances translational efficiency of a heterologous coding sequence operably linked thereto.

7. An isolated nucleic acid molecule consisting of a variant of SEQ ID NO:4; wherein the variation from SEQ ID NO:4 in said variant comprises at least one of an insertion, deletion, or substitution of one or more nucleotides, and wherein said isolated nucleic acid molecule enhances translational efficiency of a heterologous coding sequence operably linked thereto.

8. An isolated nucleic acid molecule consisting of a variant of SEQ ID NO:5; wherein the variation from SEO ID NO:5 in said variant comprises at least one of an insertion, deletion, or substitution of one or more nucleotides, and wherein said isolated nucleic acid molecule enhances translational efficiency of a heterologous coding sequence operably linked thereto.

9. An isolated nucleic acid molecule consisting of the sequence set forth in SEQ ID NO: 4.

10. An isolated nucleic acid molecule consisting of the sequence set forth in SEQ ID NO: 5.

11. A method of expressing a heterologous gene, which comprises transforming a eukaryotic cell with an expression vector comprising said heteroloaous gene operably linked to a 5' regulatory region and a 3' termination sequence wherein at least one isolated nucleic acid molecule according to any one of claims 1–10 is inserted in at least one position 5' or 3' to the heterologous gene.

12. A recombinant nucleic acid molecule comprising at least one isolated nucleic acid molecule of any of claims 1–10 and a heterologous coding sequence, wherein said isolated nucleic acid molecule is operably linked to said heterologous coding sequence.

13. A vector comprising the recombinant nucleic acid molecule of claim 12.

14. A vector according to claim 13, wherein said heteroloaous coding sequence is operably linked to a 5' regulatory region and a 3' transcription termination sequence.

15. The vector of claim 14 wherein said isolated nucleic acid molecule is placed downstream from the 5' regulatory sequence.

16. The vector of claim 14 wherein said isolated nucleic acid molecule is placed upstream from the 3' transcription termination sequence.

17. A method of expressing a heterologous gene in a eukaryotic cell which comprises transforming a eukaryotic cell with the vector of claim 14 and expressing said heterologous gene.

18. The method of claim 17, wherein the eukaryotic cell is at least one of a mammalian cell, yeast cell, or insect cell.

19. The method of claim 18, wherein the eukaryotic cell is a mammalian neuronal cell.

20. The method of claim 19, wherein the neuronal cell is a neuroblastoma cell.

21. The vector of claim 14 wherein the heterologous coding sequence codes for green fluorescent protein (GFP) derived from *Aequorea victoria*.

22. The method of claim 17, wherein the eukaryotic cell is a mammalian nonneuronal cell.

23. The method of claim 22, wherein the mammalian nonneuronal cell is selected from the group consisting of CHO cells, human fibroblast cells and a hemopoietic stem cell line.

24. A vector according to claim 13 further comprising a multiple cloning site.

25. The vector of claim 24 wherein said isolated nucleic acid molecule is placed upstream from the multiple cloning site.

26. The vector of claim 24 wherein said isolated nucleic acid molecule is placed downstream from the multiple cloning site.

27. A vector according to claim 13 wherein said heteroloaous coding sequence is a reporter gene.

* * * * *